US012774311B2

(12) United States Patent
Kim et al.

(10) Patent No.: US 12,774,311 B2
(45) Date of Patent: *Oct. 27, 2026

(54) USE OF LONG-ACTING FGF21 FUSION PROTEINS IN TREATING FGF21-ASSOCIATED DISORDERS

(71) Applicant: YUHAN CORPORATION, Seoul (KR)

(72) Inventors: Jun Hwan Kim, Seoul (KR); Seyoung Lim, Yongin-si (KR); Minji Seo, Seoul (KR); Hyun Ho Choi, Suwon-si (KR); Dohoon Kim, Yongin-si (KR); Mi Kyeong Ju, Suwon-si (KR); Ju-Young Park, Seoul (KR); Byung Hyun Choi, Suwon-si (KR); Jun Kyung Lee, Suwon-si (KR); Jong Gyun Kim, Anyang-si (KR); Su Youn Nam, Seoul (KR)

(73) Assignee: YUHAN CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/491,616

(22) Filed: Oct. 20, 2023

(65) Prior Publication Data

US 2024/0279296 A1 Aug. 22, 2024

Related U.S. Application Data

(60) Continuation of application No. 17/478,600, filed on Sep. 17, 2021, now abandoned, which is a division of application No. 15/768,616, filed as application No. PCT/KR2016/012288 on Oct. 28, 2016, now Pat. No. 11,142,557.

(30) Foreign Application Priority Data

Oct. 28, 2015 (KR) ........................ 10-2015-0150574

(51) Int. Cl.

| | |
|---|---|
| ***A61K 38/18*** | (2006.01) |
| ***A61P 1/16*** | (2006.01) |
| ***A61P 3/04*** | (2006.01) |
| ***A61P 3/10*** | (2006.01) |
| ***C07K 14/50*** | (2006.01) |

(52) U.S. Cl.

CPC ................ *C07K 14/50* (2013.01); *A61P 1/16* (2018.01); *A61P 3/04* (2018.01); *A61P 3/10* (2018.01); *A61K 38/1825* (2013.01); *C07K 2319/30* (2013.01)

(58) Field of Classification Search

None

See application file for complete search history.

(56) References Cited

U.S. PATENT DOCUMENTS

| | | | |
|---|---|---|---|
| 5,851,800 | A | 12/1998 | Adamson et al. |
| 8,034,770 | B2 | 10/2011 | Belouski et al. |
| 8,361,963 | B2 | 1/2013 | Belouski et al. |
| 8,410,051 | B2 | 4/2013 | Belouski et al. |
| 8,642,546 | B2 | 2/2014 | Belouski et al. |
| 9,023,791 | B2 | 5/2015 | Boettcher et al. |
| 9,273,106 | B2 | 3/2016 | Belouski et al. |
| 9,434,778 | B2 | 9/2016 | Morin et al. |
| 9,441,030 | B2 | 9/2016 | Song et al. |
| 9,926,351 | B2 | 3/2018 | Schellenberger et al. |
| 11,136,364 | B2 | 10/2021 | Kim et al. |
| 11,142,557 | B2 | 10/2021 | Kim et al. |
| 11,179,440 | B2 | 11/2021 | Hong et al. |
| 2009/0305986 | A1 | 12/2009 | Belouski et al. |
| 2010/0112641 | A1 | 5/2010 | Song et al. |
| 2010/0285131 | A1 | 11/2010 | Belouski et al. |
| 2011/0034373 | A1 | 2/2011 | Coskun et al. |
| 2011/0195895 | A1 | 8/2011 | Walker et al. |
| 2012/0003216 | A1 | 1/2012 | Belouski et al. |
| 2012/0035099 | A1 | 2/2012 | Garibay et al. |
| 2012/0087920 | A1 | 4/2012 | Belouski et al. |
| 2012/0093815 | A1 | 4/2012 | Belouski et al. |
| 2012/0172298 | A1 | 7/2012 | Andersen et al. |
| 2012/0238496 | A1 | 9/2012 | Fan et al. |
| 2013/0129724 | A1 | 5/2013 | Boettcher et al. |
| 2013/0190232 | A1 | 7/2013 | Tagmose et al. |
| 2013/0330336 | A1 | 12/2013 | Darling et al. |
| 2014/0073563 | A1 | 3/2014 | Boscheinen et al. |
| 2014/0213512 | A1 | 7/2014 | Ellison et al. |

(Continued)

FOREIGN PATENT DOCUMENTS

| | | |
|---|---|---|
| CN | 101993496 A | 3/2011 |
| CN | 102558358 A | 7/2012 |

(Continued)

OTHER PUBLICATIONS

Jensen et al., Circulation 129(25, supp.2): S102-S138, 2014.*
Gaich et al. (Cell Metabolism 18: 333-340, 2013).*
Fisher et al. (Diabetes 59: 2781-2789, 2010).*
European Patent Office; Communication dated Feb. 13, 2019 issued in Application No. 16860300.9.
Bernard Thorens et al., "Cloning and Functional Expression of the Human Islet GLP-1 Receptor," Diabetes, Nov. 1993, pp. 1678-1682, vol. 42.
H. Kahal et al., "Glucagon-like peptide-1 analogue, liraglutide, improves liver fibrosis markers in obese women with polycystic ovary syndrome and nonalcoholic fatty liver disease", Clinical Endocrinology, 2014, pp. 523-528, vol. 81.

(Continued)

*Primary Examiner* — Christine J Saoud

(74) *Attorney, Agent, or Firm* — Sughrue Mion, PLLC

(57) ABSTRACT

A fusion protein contains an FGF21 mutant protein and an Fc region of an immunoglobulin. The fusion protein exhibits improved pharmacological efficacy, in vivo duration and protein stability. A pharmaceutical composition containing the fusion protein as an active ingredient may be effectively used as a therapeutic agent for diabetes, obesity, dyslipidemia, metabolic syndrome, non-alcoholic fatty liver disease or non-alcoholic steatohepatitis.

4 Claims, 19 Drawing Sheets

Specification includes a Sequence Listing.

(56) References Cited

U.S. PATENT DOCUMENTS

| | | | |
|---|---|---|---|
| 2014/0243503 | A1 | 8/2014 | Belouski et al. |
| 2014/0323396 | A1 | 10/2014 | Belouski et al. |
| 2016/0168223 | A1 | 6/2016 | Belouski et al. |
| 2018/0298078 | A1 | 10/2018 | Park et al. |
| 2018/0305428 | A1 | 10/2018 | Kim et al. |
| 2019/0314452 | A1 | 10/2019 | Hong et al. |
| 2020/0024318 | A1 | 1/2020 | Kim et al. |
| 2021/0188936 | A1 | 6/2021 | Choi et al. |
| 2022/0002368 | A1 | 1/2022 | Kim et al. |

FOREIGN PATENT DOCUMENTS

| | | | |
|---|---|---|---|
| CN | 102625811 | A | 8/2012 |
| CN | 102655877 | A | 9/2012 |
| CN | 102802657 | A | 11/2012 |
| CN | 103124562 | A | 5/2013 |
| CN | 103415300 | A | 11/2013 |
| CN | 104736558 | A | 6/2015 |
| CN | 105288592 | A | 2/2016 |
| EA | 020843 | B1 | 2/2015 |
| EP | 0 306 968 | A2 | 3/1989 |
| EP | 0 345 660 | A1 | 12/1989 |
| EP | 2 548 570 | A1 | 1/2013 |
| JP | 2006-94727 | A | 4/2006 |
| JP | 2006-520186 | A | 9/2006 |
| JP | 2009-534424 | A | 9/2009 |
| JP | 2010-531134 | A | 9/2010 |
| JP | 2011-518175 | A | 6/2011 |
| JP | 2011-523561 | A | 8/2011 |
| JP | 2012-504965 | A | 3/2012 |
| JP | 2012-515747 | A | 7/2012 |
| JP | 2012-525847 | A | 10/2012 |
| JP | 2014-510707 | A | 5/2014 |
| JP | 2014-526441 | A | 10/2014 |
| JP | 2014-527986 | A | 10/2014 |
| JP | 2015-527974 | A | 9/2015 |
| JP | 2018-522147 | A | 8/2018 |
| JP | 2018-534929 | A | 11/2018 |
| JP | 2019-500013 | A | 1/2019 |
| JP | 2020-502053 | A | 1/2020 |
| JP | 2023-11644 | A | 1/2023 |
| RU | 2 741 345 | C2 | 1/2021 |
| WO | 90/02175 | A1 | 3/1990 |
| WO | 2003/011213 | A2 | 7/2002 |
| WO | 03/059934 | A2 | 7/2003 |
| WO | 2004/058800 | A2 | 7/2004 |
| WO | 2005/000892 | A2 | 1/2005 |
| WO | 2005/091944 | A2 | 10/2005 |
| WO | 2007/124463 | A1 | 11/2007 |
| WO | 2008/147143 | A2 | 12/2008 |
| WO | 2009/020802 | A2 | 2/2009 |
| WO | 2009/129379 | A1 | 10/2009 |
| WO | 2009/149171 | A2 | 12/2009 |
| WO | 2010/042747 | A2 | 4/2010 |
| WO | 2010/065439 | A1 | 6/2010 |
| WO | 2010/084169 | A2 | 7/2010 |
| WO | 2010/091122 | A1 | 8/2010 |
| WO | 2010/129503 | A1 | 11/2010 |
| WO | 2010/129600 | A2 | 11/2010 |
| WO | 2010/142665 | A1 | 12/2010 |
| WO | 2011/020319 | A1 | 2/2011 |
| WO | 2011/028229 | A1 | 3/2011 |
| WO | 2011/089170 | A1 | 7/2011 |
| WO | 2011/154349 | A2 | 12/2011 |
| WO | 2012/010553 | A1 | 1/2012 |
| WO | 2012/066075 | A1 | 5/2012 |
| WO | 2012/093127 | A2 | 7/2012 |
| WO | 2012/170438 | A2 | 12/2012 |
| WO | 2013/033452 | A2 | 3/2013 |
| WO | 2013/049234 | A2 | 4/2013 |
| WO | 2013131091 | A1 | 9/2013 |
| WO | 2013/188181 | A1 | 12/2013 |
| WO | 2014/037373 | A1 | 3/2014 |
| WO | 2014/130659 | A1 | 8/2014 |
| WO | 2015/038938 | A1 | 3/2015 |
| WO | 2016/048995 | A2 | 3/2016 |
| WO | 2016/114633 | A1 | 7/2016 |
| WO | 2017/065559 | A1 | 4/2017 |
| WO | 2017/074117 | A1 | 5/2017 |
| WO | 2017/074123 | A1 | 5/2017 |
| WO | 2018/088838 | A1 | 5/2018 |
| WO | 2018/166461 | A1 | 9/2018 |
| WO | 2018/194413 | A1 | 10/2018 |

OTHER PUBLICATIONS

Justin D. Schumacher et al., "Regulation of Hepatic Stellate Cells and Fibrogenesis by Fibroblast Growth Factors", BioMed Research International, Jan. 2016 (Posted on ResearchGate), 21 pages.

Mashkovsky M.D. Medicines, 16th ed., Revised, and add.—M.: Novaya Volna, 2012, p. 8 (2 pages total).

Yakubke H.-D et al., Amino acids, peptides, proteins.—M.: Mir, 1985, p. 92-94 (5 pages total).

English Translation of Office Action issued Jan. 28, 2021 in Russian Application No. 2019117767.

Randy Hecht et al., "Rationale-Based Engineering of a Potent Long-Acting FGF21 Analog for the Treatment of Type 2 Diabetes", PLoS One, Nov. 27, 2012, pp. 1-14, vol. 7, issue 11.

Jie Huang et al., "Development of a Novel Long-Acting Antidiabetic FGF21 Mimetic by Targeted Conjugation to a Scaffold Antibody", The Journal of Pharmacology and Experimental Therapeutics, Aug. 2013, pp. 270-280, vol. 346.

International Search Report for PCT/KR2016/012288 dated Jan. 31, 2017.

Alexei Kharitonenkov et al., "FGF-21 as a novel metabolic regulator", The Journal of Clinical Investigation, Jun. 2005, pp. 1627-1635, vol. 115, No. 6.

Michelle Orlando, "Modification of proteins and low molecular weight substances with hydroxyethyl starch (HES)", 2003, Inauguraldissertation, Giesen (191 pages).

Richard Smith et al., "FGF21 Can be Mimicked In Vitro and In Vivo by a Novel Anti-FGFR1c/β-Klotho Bispecific Protein", PLOS ONE, 2013, vol. 8, Issue 4, e61432 (11 pages total).

Xiaoying Chen et al., "Fusion Protein Linkers: Property, Design and Functionality", Adv Drug Deliv Rev., 2013, vol. 65, No. 10, pp. 1357-1369 (32 pages total).

Joel D.A. Tyndall et al., "Over One Hundred Peptide-Activated G Protein-Coupled Receptors Recognize Ligands with Turn Structure", Chem. Rev., 2005, vol. 105, No. 3, pp. 793-826 (34 pages total).

Yumi Maeda et al., "Engineering of Functional Chimeric Protein G-Vargula Luciferase", Analytical Biochemistry, 1997, vol. 249, No. 2, pp. 147-152 (6 pages total).

H-D. Jakubke et al., "I am amino acids, peptides, proteins: Per-M: Mir", 1985 (5 pages total).

H.N. Hong et al., "YH25724, a novel long-acting GLP-1/FGF21 dual agonist lowers both non-alcoholic fatty liver disease activity score and fibrosis stage in a diet-induced obese mouse model of biopsy-confirmed non-alcoholic steatohepatitis", Journal of Hepatology, 2017, vol. 66; pp. S16-S17 (2 pages total).

Wolfgang Glaesner et al., "Engineering and characterization of the long-acting glucagon-like peptide-1 analogue LY2189265, an Fc fusion protein", Diabetes/Metabolism Research and Reviews, 2010, vol. 26, pp. 287-296 (10 pages total).

Nobuhiko Tokuriki et al., "Stability effects of mutations and protein evolvability", Current Opinion in Structural Biology, 2009, vol. 19, pp. 596-604 (9 pages total).

Juqun Shen et al., "Single Variable Domain-IgG Fusion: A Novel Recombinant Approach to Fc Domain-Containing Bispecific Antibodies", The Journal of Biological Chemistry, Apr. 21, 2006, vol. 281, No. 16, pp. 10706-10714 (9 pages total).

N.E. Kuzmina et al., "Quantitative Determination of the Mean Molecular Mass of Dextrans by Means of Diffusion-Ordered NMR Spectroscopy", Journal of Analytical Chemistry, 2014, vol. 69, No. 10, pp. 1047-1053 (17 pages total).

(56) References Cited

OTHER PUBLICATIONS

Jonathan W. Neidigh et al., "Exendin-4 and Glucagon-like-peptide-1: NMR Structural Comparisons in the Solution and Micelle-Associated States", Biochemistry, 2001, vol. 40, No. 44, pp. 13188-13200 (13 pages total).
Andrea Bedoya-Lopez et al., "Effect of Temperature Downshift on the Transcriptomic Responses of Chinese Hamster Ovary Cells Using Recombinant Human Tissue Plasminogen Activator Production Culture", PLOS ONE 11(3): e0151529, Mar. 18, 2016, pp. 1-26 (26 pages total).
J. Pedro Menvielle, et al., "Dual Role of Dextran Sulfate 5000 Da as Anti-Apoptotic and Pro-Autophagy Agent", Molecular Biotechnology, Nov. 2012 (11 pages total).

* cited by examiner

| | $EC_{50}$(nM) |
|---|---|
| DFD4 | 13.97 |
| DFD5 | 20.19 |
| DFD6 | 23.73 |
| DFD7 | 14.73 |
| DFD9 | 17.13 |
| DFD13 | 15.31 |

| | $EC_{50}$(nM) |
|---|---|
| DFD6 | 18.41 |
| DFD13 | 17.28 |
| DFD18 | 25.52 |
| DFD72 | 28.13 |
| DFD73 | 16.96 |
| DFD74 | 19.45 |

| | $EC_{50}$(nM) |
|---|---|
| DFD6 | 12.61 |
| DFD6(E-coli) | 14.49 |

| | $EC_{50}$(nM) |
|---|---|
| DFD3 | 15.69 |
| DFD4 | 23.37 |

| | $EC_{50}$(nM) |
|---|---|
| DFD1 | 9.77 |
| DFD13 | 14.18 |

| | $EC_{50}$(nM) |
|---|---|
| DFD1 | 23.44 |
| Fc-FGF21(Lilly) | 10.95 |
| RGE(Amgen) | 23.81 |

| | RT | Area | %Area | Height |
|---|---|---|---|---|
| 1 | 6.425 | 46359 | 0.93 | 1520 |
| 2 | 7.136 | 4940917 | 99.07 | 234651 |

| | RT | Area | %Area | Height |
|---|---|---|---|---|
| 1 | 6.474 | 28735 | 0.60 | 984 |
| 2 | 7.174 | 4789139 | 99.40 | 232719 |

```
                              SEQUENCE LISTING


Sequence total quantity: 57
SEQ ID NO: 1            moltype = AA  length = 181
FEATURE                 Location/Qualifiers
REGION                  1..181
                        note = human FGF21
source                  1..181
                        mol_type = protein
                        organism = Homo sapiens
SEQUENCE: 1
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
NKSPHRDPAP RGPARFLPLP GLPPALPEPP GILAPQPPDV GSSDPLSMVG PSQGRSPSYA  180
S                                                                  181

SEQ ID NO: 2            moltype = AA  length = 30
FEATURE                 Location/Qualifiers
REGION                  1..30
                        note = linker
source                  1..30
                        mol_type = protein
                        organism = synthetic construct
SEQUENCE: 2
AKATTAPATT RNTGRGGEEK KKEKEKEEQE                                   30

SEQ ID NO: 3            moltype = AA  length = 17
FEATURE                 Location/Qualifiers
REGION                  1..17
                        note = linker
source                  1..17
                        mol_type = protein
                        organism = synthetic construct
SEQUENCE: 3
AKATTAPATT RNTGRGG                                                 17

SEQ ID NO: 4            moltype = AA  length = 15
FEATURE                 Location/Qualifiers
REGION                  1..15
                        note = linker
source                  1..15
                        mol_type = protein
                        organism = synthetic construct
SEQUENCE: 4
GGGGSGGGGS GGGGS                                                   15

SEQ ID NO: 5            moltype = AA  length = 16
FEATURE                 Location/Qualifiers
REGION                  1..16
                        note = linker
source                  1..16
                        mol_type = protein
                        organism = synthetic construct
SEQUENCE: 5
GGGGSGGGGS GGGGSA                                                  16

SEQ ID NO: 6            moltype = AA  length = 181
FEATURE                 Location/Qualifiers
REGION                  1..181
                        note = FGF21 variant
source                  1..181
                        mol_type = protein
                        organism = synthetic construct
SEQUENCE: 6
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFREEIR PDGYNVYQSE AHGLPLHLPG  120
NKSPHRDPAP RGPARFLPLP GLPPALPEPP GILAPQPPDV GSSDPLSMVG PSQGRSPSYA  180
S                                                                  181

SEQ ID NO: 7            moltype = AA  length = 182
FEATURE                 Location/Qualifiers
REGION                  1..182
                        note = FGF21 variant
source                  1..182
```

```
                        mol_type = protein
                        organism = synthetic construct
SEQUENCE: 7
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
NKSPHRDPAP RGPARFLPLP GLPPALPEPP GILAPQPPDV GSSDPLSMVT GLEAVRSPSY  180
AS                                                                182

SEQ ID NO: 8            moltype = AA  length = 182
FEATURE                 Location/Qualifiers
REGION                  1..182
                        note = FGF21 variant
source                  1..182
                        mol_type = protein
                        organism = synthetic construct
SEQUENCE: 8
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
NKSPHRDPAP RGPARFLPLP GLPPALPEPP GILAPQPPDV GSSDPLSMVT GLEANRSPSY  180
AS                                                                182

SEQ ID NO: 9            moltype = AA  length = 181
FEATURE                 Location/Qualifiers
REGION                  1..181
                        note = FGF21 variant
source                  1..181
                        mol_type = protein
                        organism = synthetic construct
SEQUENCE: 9
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
NKSPHRDPAP RGPARFLPLP GLPPALPEPP GILAPQPPDV GSSDPLSMVN PSQGRSPSYA  180
S                                                                 181

SEQ ID NO: 10           moltype = AA  length = 181
FEATURE                 Location/Qualifiers
REGION                  1..181
                        note = FGF21 variant
source                  1..181
                        mol_type = protein
                        organism = synthetic construct
SEQUENCE: 10
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
NKSPHRDPAP RGPARFLPLP GLPPALPEPP GILAPQPPDV GSSDPLSMVG PSQNRSPSYA  180
S                                                                 181

SEQ ID NO: 11           moltype = AA  length = 182
FEATURE                 Location/Qualifiers
REGION                  1..182
                        note = FGF21 variant
source                  1..182
                        mol_type = protein
                        organism = synthetic construct
SEQUENCE: 11
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFREEIR PDGYNVYQSE AHGLPLHLPG  120
NKSPHRDPAP RGPARFLPLP GLPPALPEPP GILAPQPPDV GSSDPLSMVT GLEAVRSPSY  180
AS                                                                182

SEQ ID NO: 12           moltype = AA  length = 182
FEATURE                 Location/Qualifiers
REGION                  1..182
                        note = FGF21 variant
source                  1..182
                        mol_type = protein
                        organism = synthetic construct
SEQUENCE: 12
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFREEIR PDGYNVYQSE AHGLPLHLPG  120
NKSPHRDPAP RGPARFLPLP GLPPALPEPP GILAPQPPDV GSSDPLSMVT GLEANRSPSY  180
AS                                                                182

SEQ ID NO: 13           moltype = AA  length = 181
FEATURE                 Location/Qualifiers
REGION                  1..181
                        note = FGF21 variant
source                  1..181
                        mol_type = protein
```

```
                         organism = synthetic construct
SEQUENCE: 13
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFREEIR PDGYNVYQSE AHGLPLHLPG  120
NKSPHRDPAP RGPARFLPLP GLPPALPEPP GILAPQPPDV GSSDPLSMVN PSQGRSPSYA  180
S                                                                 181

SEQ ID NO: 14            moltype = AA  length = 181
FEATURE                  Location/Qualifiers
REGION                   1..181
                         note = FGF21 variant
source                   1..181
                         mol_type = protein
                         organism = synthetic construct
SEQUENCE: 14
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFREEIR PDGYNVYQSE AHGLPLHLPG  120
NKSPHRDPAP RGPARFLPLP GLPPALPEPP GILAPQPPDV GSSDPLSMVG PSQNRSPSYA  180
S                                                                 181

SEQ ID NO: 15            moltype = AA  length = 181
FEATURE                  Location/Qualifiers
REGION                   1..181
                         note = FGF21 variant
source                   1..181
                         mol_type = protein
                         organism = synthetic construct
SEQUENCE: 15
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFREEIR PDGYNVYQSE AHGLPLHLPG  120
NKSPHRDPAP RGPARFLPLP GLPPALPEPP GILAPQPPDV GSSDPLSMVG PSQGRSPSYE  180
S                                                                 181

SEQ ID NO: 16            moltype = AA  length = 182
FEATURE                  Location/Qualifiers
REGION                   1..182
                         note = FGF21 variant
source                   1..182
                         mol_type = protein
                         organism = synthetic construct
SEQUENCE: 16
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
NKSPHRDPAP RGPARFLPLP GLPPALPEPP GILAPQPPDV GSSDPLSMVT GLEAVRSPSY  180
ES                                                                182

SEQ ID NO: 17            moltype = AA  length = 182
FEATURE                  Location/Qualifiers
REGION                   1..182
                         note = FGF21 variant
source                   1..182
                         mol_type = protein
                         organism = synthetic construct
SEQUENCE: 17
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
NKSPHRDPAP RGPARFLPLP GLPPALPEPP GILAPQPPDV GSSDPLSMVT GLEANRSPSY  180
ES                                                                182

SEQ ID NO: 18            moltype = AA  length = 181
FEATURE                  Location/Qualifiers
REGION                   1..181
                         note = FGF21 variant
source                   1..181
                         mol_type = protein
                         organism = synthetic construct
SEQUENCE: 18
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
NKSPHRDPAP RGPARFLPLP GLPPALPEPP GILAPQPPDV GSSDPLSMVN PSQGRSPSYE  180
S                                                                 181

SEQ ID NO: 19            moltype = AA  length = 181
FEATURE                  Location/Qualifiers
REGION                   1..181
                         note = FGF21 variant
source                   1..181
                         mol_type = protein
                         organism = synthetic construct
```

-continued

```
SEQUENCE: 19
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG  120
NKSPHRDPAP RGPARFLPLP GLPPALPEPP GILAPQPPDV GSSDPLSMVG PSQNRSPSYE  180
S                                                                 181

SEQ ID NO: 20          moltype = AA  length = 182
FEATURE                Location/Qualifiers
REGION                 1..182
                       note = FGF21 variant
source                 1..182
                       mol_type = protein
                       organism = synthetic construct
SEQUENCE: 20
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFREEIR PDGYNVYQSE AHGLPLHLPG  120
NKSPHRDPAP RGPARFLPLP GLPPALPEPP GILAPQPPDV GSSDPLSMVT GLEAVRSPSY  180
ES                                                                182

SEQ ID NO: 21          moltype = AA  length = 182
FEATURE                Location/Qualifiers
REGION                 1..182
                       note = FGF21 variant
source                 1..182
                       mol_type = protein
                       organism = synthetic construct
SEQUENCE: 21
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFREEIR PDGYNVYQSE AHGLPLHLPG  120
NKSPHRDPAP RGPARFLPLP GLPPALPEPP GILAPQPPDV GSSDPLSMVT GLEANRSPSY  180
ES                                                                182

SEQ ID NO: 22          moltype = AA  length = 181
FEATURE                Location/Qualifiers
REGION                 1..181
                       note = FGF21 variant
source                 1..181
                       mol_type = protein
                       organism = synthetic construct
SEQUENCE: 22
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFREEIR PDGYNVYQSE AHGLPLHLPG  120
NKSPHRDPAP RGPARFLPLP GLPPALPEPP GILAPQPPDV GSSDPLSMVN PSQGRSPSYE  180
S                                                                 181

SEQ ID NO: 23          moltype = AA  length = 181
FEATURE                Location/Qualifiers
REGION                 1..181
                       note = FGF21 variant
source                 1..181
                       mol_type = protein
                       organism = synthetic construct
SEQUENCE: 23
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFREEIR PDGYNVYQSE AHGLPLHLPG  120
NKSPHRDPAP RGPARFLPLP GLPPALPEPP GILAPQPPDV GSSDPLSMVG PSQNRSPSYE  180
S                                                                 181

SEQ ID NO: 24          moltype = AA  length = 229
FEATURE                Location/Qualifiers
REGION                 1..229
                       note = Human IgG4 Fc
source                 1..229
                       mol_type = protein
                       organism = synthetic construct
SEQUENCE: 24
ESKYGPPCPS CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 25          moltype = AA  length = 228
FEATURE                Location/Qualifiers
REGION                 1..228
                       note = Human IgG4 Fc variant
source                 1..228
                       mol_type = protein
                       organism = synthetic construct
SEQUENCE: 25
```

```
ESKYGPPCPP CPAPEAAGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLG              228

SEQ ID NO: 26          moltype = AA  length = 223
FEATURE                Location/Qualifiers
REGION                 1..223
                       note = Hybrid Fc variant
source                 1..223
                       mol_type = protein
                       organism = synthetic construct
SEQUENCE: 26
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGK                   223

SEQ ID NO: 27          moltype = AA  length = 435
FEATURE                Location/Qualifiers
REGION                 1..435
                       note = modified FGF21 variant connected to hybrid Fc
source                 1..435
                       mol_type = protein
                       organism = synthetic construct
SEQUENCE: 27
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKAKATTAP ATTRNTGRGG  240
EEKKKEKEKE EQEHPIPDSS PLLQFGGQVR QRYLYTDDAQ QTEAHLEIRE DGTVGGAADQ  300
SPESLLQLKA LKPGVIQILG VKTSRFLCQR PDGALYGSLH FDPEACSFRE EIRPDGYNVY  360
QSEAHGLPLH LPGNKSPHRD PAPRGPARFL PLPGLPPALP EPPGILAPQP PDVGSSDPLS  420
MVTGLEAVRS PSYAS                                                  435

SEQ ID NO: 28          moltype = AA  length = 422
FEATURE                Location/Qualifiers
REGION                 1..422
                       note = modified FGF21 variant connected to hybrid Fc
source                 1..422
                       mol_type = protein
                       organism = synthetic construct
SEQUENCE: 28
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKAKATTAP ATTRNTGRGG  240
HPIPDSSPLL QFGGQVRQRY LYTDDAQQTE AHLEIREDGT VGGAADQSPE SLLQLKALKP  300
GVIQILGVKT SRFLCQRPDG ALYGSLHFDP EACSFRELLL EDGYNVYQSE AHGLPLHLPG  360
NKSPHRDPAP RGPARFLPLP GLPPALPEPP GILAPQPPDV GSSDPLSMVT GLEAVRSPSY  420
AS                                                                422

SEQ ID NO: 29          moltype = AA  length = 420
FEATURE                Location/Qualifiers
REGION                 1..420
                       note = modified FGF21 variant connected to hybrid Fc
source                 1..420
                       mol_type = protein
                       organism = synthetic construct
SEQUENCE: 29
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKGGGGSGG GGSGGGGSHP  240
IPDSSPLLQF GGQVRQRYLY TDDAQQTEAH LEIREDGTVG GAADQSPESL LQLKALKPGV  300
IQILGVKTSR FLCQRPDGAL YGSLHFDPEA CSFRELLLED GYNVYQSEAH GLPLHLPGNK  360
SPHRDPAPRG PARFLPLPGL PPALPEPPGI LAPQPPDVGS SDPLSMVTGL EAVRSPSYAS  420

SEQ ID NO: 30          moltype = AA  length = 420
FEATURE                Location/Qualifiers
REGION                 1..420
                       note = modified FGF21 variant connected to hybrid Fc
source                 1..420
                       mol_type = protein
                       organism = synthetic construct
SEQUENCE: 30
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
```

```
FLYSRLTVDK SRWQEGNVFS CSVMHEALHN HYTQKSLSLS LGKGGGGSGG GGSGGGGSHP  240
IPDSSPLLQF GGQVRQRYLY TDDAQQTEAH LEIREDGTVG GAADQSPESL LQLKALKPGV  300
IQILGVKTSR FLCQRPDGAL YGSLHFDPEA CSFRELLLED GYNVYQSEAH GLPLHLPGNK  360
SPHRDPAPRG PARFLPLPGL PPALPEPPGI LAPQPPDVGS SDPLSMVTGL EANRSPSYAS  420

SEQ ID NO: 31          moltype = AA  length = 419
FEATURE                Location/Qualifiers
REGION                 1..419
                       note = modified FGF21 variant connected to hybrid Fc
source                 1..419
                       mol_type = protein
                       organism = synthetic construct
SEQUENCE: 31
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKGGGGSGG GGSGGGGSHP  240
IPDSSPLLQF GGQVRQRYLY TDDAQQTEAH LEIREDGTVG GAADQSPESL LQLKALKPGV  300
IQILGVKTSR FLCQRPDGAL YGSLHFDPEA CSFRELLLED GYNVYQSEAH GLPLHLPGNK  360
SPHRDPAPRG PARFLPLPGL PPALPEPPGI LAPQPPDVGS SDPLSMVNPS QGRSPSYAS   419

SEQ ID NO: 32          moltype = AA  length = 419
FEATURE                Location/Qualifiers
REGION                 1..419
                       note = modified FGF21 variant connected to hybrid Fc
source                 1..419
                       mol_type = protein
                       organism = synthetic construct
SEQUENCE: 32
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKGGGGSGG GGSGGGGSHP  240
IPDSSPLLQF GGQVRQRYLY TDDAQQTEAH LEIREDGTVG GAADQSPESL LQLKALKPGV  300
IQILGVKTSR FLCQRPDGAL YGSLHFDPEA CSFRELLLED GYNVYQSEAH GLPLHLPGNK  360
SPHRDPAPRG PARFLPLPGL PPALPEPPGI LAPQPPDVGS SDPLSMVNPS QGRSPSYAS   419

SEQ ID NO: 33          moltype = AA  length = 419
FEATURE                Location/Qualifiers
REGION                 1..419
                       note = modified FGF21 variant connected to hybrid Fc
source                 1..419
                       mol_type = protein
                       organism = synthetic construct
SEQUENCE: 33
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKGGGGSGG GGSGGGGSHP  240
IPDSSPLLQF GGQVRQRYLY TDDAQQTEAH LEIREDGTVG GAADQSPESL LQLKALKPGV  300
IQILGVKTSR FLCQRPDGAL YGSLHFDPEA CSFRELLLED GYNVYQSEAH GLPLHLPGNK  360
SPHRDPAPRG PARFLPLPGL PPALPEPPGI LAPQPPDVGS SDPLSMVGPS QNRSPSYAS   419

SEQ ID NO: 34          moltype = AA  length = 419
FEATURE                Location/Qualifiers
REGION                 1..419
                       note = modified FGF21 variant connected to hybrid Fc
source                 1..419
                       mol_type = protein
                       organism = synthetic construct
SEQUENCE: 34
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKGGGGSGG GGSGGGGSHP  240
IPDSSPLLQF GGQVRQRYLY TDDAQQTEAH LEIREDGTVG GAADQSPESL LQLKALKPGV  300
IQILGVKTSR FLCQRPDGAL YGSLHFDPEA CSFRELLLED GYNVYQSEAH GLPLHLPGNK  360
SPHRDPAPRG PARFLPLPGL PPALPEPPGI LAPQPPDVGS SDPLSMVGPS QGRSPSYAS   419

SEQ ID NO: 35          moltype = AA  length = 420
FEATURE                Location/Qualifiers
REGION                 1..420
                       note = modified FGF21 variant connected to hybrid Fc
source                 1..420
                       mol_type = protein
                       organism = synthetic construct
SEQUENCE: 35
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
```

```
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKGGGGSGG GGSGGGGSHP  240
IPDSSPLLQF GGQVRQRYLY TDDAQQTEAH LEIREDGTVG GAADQSPESL LQLKALKPGV  300
IQILGVKTSR FLCQRPDGAL YGSLHFDPEA CSFREEIRPD GYNVYQSEAH GLPLHLPGNK  360
SPHRDPAPRG PARFLPLPGL PPALPEPPGI LAPQPPDVGS SDPLSMVTGL EAVRSPSYAS  420

SEQ ID NO: 36          moltype = AA  length = 420
FEATURE                Location/Qualifiers
REGION                 1..420
                       note = modified FGF21 variant connected to hybrid Fc
source                 1..420
                       mol_type = protein
                       organism = synthetic construct
SEQUENCE: 36
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKGGGGSGG GGSGGGGSHP  240
IPDSSPLLQF GGQVRQRYLY TDDAQQTEAH LEIREDGTVG GAADQSPESL LQLKALKPGV  300
IQILGVKTSR FLCQRPDGAL YGSLHFDPEA CSFREEIRPD GYNVYQSEAH GLPLHLPGNK  360
SPHRDPAPRG PARFLPLPGL PPALPEPPGI LAPQPPDVGS SDPLSMVTGL EAVRSPSYES  420

SEQ ID NO: 37          moltype = AA  length = 420
FEATURE                Location/Qualifiers
REGION                 1..420
                       note = modified FGF21 variant connected to hybrid Fc
source                 1..420
                       mol_type = protein
                       organism = synthetic construct
SEQUENCE: 37
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKGGGGSGG GGSGGGGSHP  240
IPDSSPLLQF GGQVRQRYLY TDDAQQTEAH LEIREDGTVG GAADQSPESL LQLKALKPGV  300
IQILGVKTSR FLCQRPDGAL YGSLHFDPEA CSFREEIRPD GYNVYQSEAH GLPLHLPGNK  360
SPHRDPAPRG PARFLPLPGL PPALPEPPGI LAPQPPDVGS SDPLSMVTGL EANRSPSYES  420

SEQ ID NO: 38          moltype = AA  length = 419
FEATURE                Location/Qualifiers
REGION                 1..419
                       note = modified FGF21 variant connected to hybrid Fc
source                 1..419
                       mol_type = protein
                       organism = synthetic construct
SEQUENCE: 38
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKGGGGSGG GGSGGGGSHP  240
IPDSSPLLQF GGQVRQRYLY TDDAQQTEAH LEIREDGTVG GAADQSPESL LQLKALKPGV  300
IQILGVKTSR FLCQRPDGAL YGSLHFDPEA CSFREEIRPD GYNVYQSEAH GLPLHLPGNK  360
SPHRDPAPRG PARFLPLPGL PPALPEPPGI LAPQPPDVGS SDPLSMVNPS QGRSPSYAS   419

SEQ ID NO: 39          moltype = AA  length = 419
FEATURE                Location/Qualifiers
REGION                 1..419
                       note = modified FGF21 variant connected to hybrid Fc
source                 1..419
                       mol_type = protein
                       organism = synthetic construct
SEQUENCE: 39
ETKTPECPSH TQPLGVFLFP PKPKDTLMIS RTPEVTCVVV DVSQEDPEVQ FNWYVDGVEV  60
HNAKTKPREE QFNSTYRVVS VLTVLHQDWL NGKEYKCKVS NKGLPSSIEK TISKAKGQPR  120
EPQVYTLPPS QEEMTKNQVS LTCLVKGFYP SDIAVEWESN GQPENNYKTT PPVLDSDGSF  180
FLYSRLTVDK SRWQEGNVFS CSVMHEALHN HYTQKSLSLS LGKGGGGSGG GGSGGGGSHP  240
IPDSSPLLQF GGQVRQRYLY TDDAQQTEAH LEIREDGTVG GAADQSPESL LQLKALKPGV  300
IQILGVKTSR FLCQRPDGAL YGSLHFDPEA CSFREEIRPD GYNVYQSEAH GLPLHLPGNK  360
SPHRDPAPRG PARFLPLPGL PPALPEPPGI LAPQPPDVGS SDPLSMVNPS QGRSPSYES   419

SEQ ID NO: 40          moltype = AA  length = 423
FEATURE                Location/Qualifiers
REGION                 1..423
                       note = RGE(Amgen)
source                 1..423
                       mol_type = protein
                       organism = synthetic construct
SEQUENCE: 40
DKTHTCPPCP APELLGGPSV FLFPPKPKDT LMISRTPEVT CVVVDVSHED PEVKFNWYVD  60
```

```
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGG GSGGGGSGGG  240
GSHPIPDSSP LLQFGGQVRQ RYLYTDDAQQ TEAHLEIRED GTVGGAADQS PESLLQLKAL  300
KPGVIQILGV KTSRFLCQRP DGALYGSLHF DPEACSFRER LLEDGYNVYQ SEAHGLPLHL  360
PGNKSPHRDP APRGPARFLP LPGLPPALPE PPGILAPQPP DVGSSDPLSM VGGSQGRSPS  420
YES                                                               423

SEQ ID NO: 41          moltype = AA  length = 424
FEATURE                Location/Qualifiers
REGION                 1..424
                       note = FGF21 connected to Fc(Lilly)
source                 1..424
                       mol_type = protein
                       organism = synthetic construct
SEQUENCE: 41
ESKYGPPCPP CPAPEAAGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGGG GGSGGGGSGG  240
GGSAHPIPDS SPLLQFGGQV RQRYLYTDDA QQTECHLEIR EDGTVGCAAD QSPESLLQLK  300
ALKPGVIQIL GVKTSRFLCQ RPDGALYGSL HFDPEACSFR EDLKEDGYNV YQSEAHGLPL  360
HLPGDKSPHR KPAPRGPARF LPLPGLPPAL PEPPGILAPQ PPDVGSSDPL RLVEPSQLRS  420
PSFE                                                              424

SEQ ID NO: 42          moltype = AA  length = 4
FEATURE                Location/Qualifiers
REGION                 1..4
                       note = FGF21 variant
source                 1..4
                       mol_type = protein
                       organism = synthetic construct
SEQUENCE: 42
EIRP                                                              4

SEQ ID NO: 43          moltype = AA  length = 6
FEATURE                Location/Qualifiers
REGION                 1..6
                       note = FGF21 variant
source                 1..6
                       mol_type = protein
                       organism = synthetic construct
SEQUENCE: 43
TGLEAV                                                            6

SEQ ID NO: 44          moltype = AA  length = 6
FEATURE                Location/Qualifiers
REGION                 1..6
                       note = FGF21 variant
source                 1..6
                       mol_type = protein
                       organism = synthetic construct
SEQUENCE: 44
TGLEAN                                                            6

SEQ ID NO: 45          moltype = DNA  length = 1305
FEATURE                Location/Qualifiers
source                 1..1305
                       mol_type = other DNA
                       organism = synthetic construct
CDS                    1..1305
                       note = nucleic acid molecule coding for DFD1
SEQUENCE: 45
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tttacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
ctgggcaaag ccaaggctac cacagcaccc gccactaccc ggaacaccgg tagaggggga  720
gaggaaaaga agaaagagaa ggaaaaagag gaacaggagc atcccatccc tgactccagt  780
cctctcctgc aattcggggg ccaagtccgg cagcggtacc tctacacaga tgatgctcag  840
cagacagaag cccacctgga gatcagggag gatgggaccg tgggggcgc tgctgaccag  900
agccccgaaa gtctcctgca gctgaaagcc ttgaagcctg gagttattca aatcttggga  960
```

-continued

```
gtcaagacta gtaggttcct gtgccagcgg ccagatgggg ccctgtatgg atctctccat  1020
tttgaccctg aggcctgcag cttccgggag gagatcagac ccgacggata caatgtttac  1080
cagtccgaag cccacggcct ccctctgcat ctgcccggga acaagtctcc tcaccgggac  1140
cctgccccca gaggacctgc tcgcttcctg ccactcccag gcctgccccc cgcattgcct  1200
gagccacccg gaatcctggc cccccagccc cctgatgtgg gatcctctga ccctctgagc  1260
atggtgacag gcctggaggc cgtgagaagc cccagctacg cttcc                 1305

SEQ ID NO: 46          moltype = DNA  length = 1266
FEATURE                Location/Qualifiers
CDS                    1..1266
                       note = nucleic acid molecule coding for DFD3
source                 1..1266
                       mol_type = other DNA
                       organism = synthetic construct
SEQUENCE: 46
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tgtacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
ctgggcaaag ccaaggctac cacagcaccc gccactacca gaaacacagg caggggggga  720
catcccatcc ctgactccag tcctctcctg caattcgggg gccaagtccg gcagcggtac  780
ctctacacag atgatgctca gcagacagaa gcccacctgg agatcaggga ggatgggacc  840
gtggggggcg ctgctgacca gagccccgaa agtctcctgc agctgaaagc cttgaagcct  900
ggagttattc aaatcttggg agtcaagact agtaggttcc tgtgccagcg gccagatggg  960
gccctgtatg gatctctcca ttttgaccct gaggcctgca gcttccggga gctgcttctt  1020
gaggacggat acaatgttta ccagtccgaa gcccacggcc tccctctgca tctgcccggg  1080
aacaagtctc ctcaccggga ccctgccccc agaggacctg ctcgcttcct gccactccca  1140
ggcctgcccc ccgcattgcc tgagccaccc ggaatcctgg ccccccagcc ccctgatgtg  1200
ggatcctctg accctctgag catggtgaca ggcctggagg ccgtgagaag ccccagctac  1260
gcttcc                                                             1266

SEQ ID NO: 47          moltype = DNA  length = 1260
FEATURE                Location/Qualifiers
CDS                    1..1260
                       note = ucleic acid molecule coding for DFD4
source                 1..1260
                       mol_type = other DNA
                       organism = synthetic construct
SEQUENCE: 47
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tgtacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
ctgggcaaag gcgggggagg cagcggggga ggcgggtccg gaggcggggg atctcatccc  720
atccctgact ccagtcctct cctgcaattc gggggccaag tccggcagcg gtacctctac  780
acagatgatg ctcagcagac agaagcccac ctggagatca gggaggatgg gaccgtgggg  840
ggcgctgctg accagagccc cgaaagtctc ctgcagctga aagccttgaa gcctggagtt  900
attcaaatct tgggagtcaa gactagtagg ttcctgtgcc agcggccaga tggggccctg  960
tatggatctc tccattttga ccctgaggcc tgcagcttcc gggagctgct tcttgaggac  1020
ggatacaatg tttaccagtc cgaagcccac ggcctccctc tgcatctgcc cgggaacaag  1080
tctcctcacc gggaccctgc ccccagagga cctgctcgct tcctgccact cccaggcctg  1140
ccccccgcat tgcctgagcc acccggaatc ctggcccccc agccccctga tgtgggatcc  1200
tctgaccctc tgagcatggt gacaggcctg gaggccgtga gaagccccag ctacgcttcc  1260

SEQ ID NO: 48          moltype = DNA  length = 1260
FEATURE                Location/Qualifiers
CDS                    1..1260
                       note = ucleic acid molecule coding for DFD5
source                 1..1260
                       mol_type = other DNA
                       organism = synthetic construct
SEQUENCE: 48
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
```

```
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tgtacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
ctgggcaaag gcgggggagg cagcggggga ggcgggtccg gaggcggggg atctcatccc  720
atccctgact ccagtcctct cctgcaattc gggggccaag tccggcagcg gtacctctac  780
acagatgatg ctcagcagac agaagcccac ctggagatca gggaggatgg gaccgtgggg  840
ggcgctgctg accagagccc cgaaagtctc ctgcagctga aagccttgaa gcctggagtt  900
attcaaatct tgggagtcaa gactagtagg ttcctgtgcc agcggccaga tggggccctg  960
tatggatctc tccattttga ccctgaggcc tgcagcttcc gggagctgct tcttgaggac  1020
ggatacaatg tttaccagtc cgaagcccac ggcctccctc tgcatctgcc cgggaacaag  1080
tctcctcacc gggaccctgc ccccagagga cctgctcgct tcctgccact cccaggcctg  1140
ccccccgcat tgcctgagcc acccggaatc ctggcccccc agccccctga tgtgggatcc  1200
tctgaccctc tgagcatggt gacaggcctg gaggccaaca gaagccccag ctacgcttcc  1260
```

```
SEQ ID NO: 49          moltype = DNA  length = 1257
FEATURE                Location/Qualifiers
CDS                    1..1257
                       note = ucleic acid molecule coding for DFD6
source                 1..1257
                       mol_type = other DNA
                       organism = synthetic construct
SEQUENCE: 49
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tgtacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
ctgggcaaag gcgggggagg cagcggggga ggcgggtccg gaggcggggg atctcatccc  720
atccctgact ccagtcctct cctgcaattc gggggccaag tccggcagcg gtacctctac  780
acagatgatg ctcagcagac agaagcccac ctggagatca gggaggatgg gaccgtgggg  840
ggcgctgctg accagagccc cgaaagtctc ctgcagctga aagccttgaa gcctggagtt  900
attcaaatct tgggagtcaa gactagtagg ttcctgtgcc agcggccaga tggggccctg  960
tatggatctc tccattttga ccctgaggcc tgcagcttcc gggagctgct tcttgaggac  1020
ggatacaatg tttaccagtc cgaagcccac ggcctccctc tgcatctgcc cgggaacaag  1080
tctcctcacc gggaccctgc ccccagagga cctgctcgct tcctgccact cccaggcctg  1140
ccccccgcat tgcctgagcc acccggaatc ctggcccccc agccccctga tgtgggatcc  1200
tctgaccctc tgagcatggt gaacccttcc cagggcagaa gccccagcta cgcttcc     1257
```

```
SEQ ID NO: 50          moltype = DNA  length = 1257
FEATURE                Location/Qualifiers
CDS                    1..1257
                       note = nucleic acid molecule coding for DFD6_E-coli
source                 1..1257
                       mol_type = other DNA
                       organism = synthetic construct
SEQUENCE: 50
gagaccaaaa ccccggaatg cccttcgcat acgcagcctt tgggtgtctt tctctttcca  60
ccaaagccga aagatacgct tatgatctct cgtacgccag aagttacctg cgtagtggtc  120
gatgtttcac aggaagatcc cgaagtacag tttaattggt acgtagacgg tgtagaagtc  180
cataatgcta aaacaaaacc gagagaagaa cagtttaatt caacgtatcg ggtggttagc  240
gttctgaccg ttctgcatca agattggctg aacgggaaag aatataaatg caaagtaagc  300
aataaagggc tgccaagctc tatcgaaaag actatatcca aggcaaaagg acaaccacgt  360
gagccgcaag tttacacatt gcctccatct caggaggaaa tgacaaaaaa tcaggtttcg  420
ttaacctgtc ttgttaaggg tttttatcct agtgatattg cagttgaatg ggaatcaaat  480
ggtcagccgg aaaacaatta taaaactact ccgcctgttc tagattctga cggttcattc  540
ttcttgtatt cgcggctcac tgttgataaa tctcgttggc aggagggtaa tgtattcagc  600
tgtagcgtta tgcacgaagc actgcacaac cattacaccc agaaaagctt gagcttaagc  660
ctgggtaaag gtggtggtgg tagtggtgga ggaggttcag gtggtggtgg tagccatcct  720
atcccagata gttctccgct tctgcagttt gggggtcaag tgcgacaacg ttatctgtat  780
actgatgatg cacagcaaac cgaagcacat cttgaaattc gtgaagacgg tacagttgga  840
ggtgcagcag atcaatcccc ggagtcgctg ttacagttga aagcgctgaa accgggtgtt  900
atacagattc tgggtgttaa aacatcacgt tttctttgtc agcgtcccga tggggcttta  960
tatgggtctc tgcatttcga cccagaagct tgttcttttc gtgaactgct tctggaagac  1020
ggctataatg tttatcaaag tgaagcacat ggtctgccat tacatctgcc gggtaacaaa  1080
tcaccacacc gtgatcctgc accgagaggt ccagctcgtt ttttacctct gcccggtcta  1140
cccccggcat tacccgaacc acctgggatt ctggcaccgc aaccgcctga tgttggaagc  1200
agtgatccgt taagtatggt taacccgagt cagggtagga gccccagcta tgcgtca     1257
```

```
SEQ ID NO: 51          moltype = DNA  length = 1257
FEATURE                Location/Qualifiers
CDS                    1..1257
                       note = nucleic acid molecule coding for DFD7
source                 1..1257
                       mol_type = other DNA
                       organism = synthetic construct
SEQUENCE: 51
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tgtacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
ctgggcaaag gcgggggagg cagcggggga ggcgggtccg gaggcggggg atctcatccc  720
atccctgact ccagtcctct cctgcaattc gggggccaag tccggcagcg gtacctctac  780
acagatgatg ctcagcagac agaagcccac ctggagatca gggaggatgg gaccgtgggg  840
ggcgctgctg accagagccc cgaaagtctc ctgcagctga aagccttgaa gcctggagtt  900
attcaaatct tgggagtcaa gactagtagg ttcctgtgcc agcggccaga tggggccctg  960
tatggatctc tccattttga ccctgaggcc tgcagcttcc gggagctgct tcttgaggac  1020
ggatacaatg tttaccagtc cgaagcccac ggcctccctc tgcatctgcc cgggaacaag  1080
tctcctcacc gggaccctgc ccccagagga cctgctcgct tcctgccact cccaggcctg  1140
ccccccgcat tgcctgagcc acccggaatc ctggcccccc agccccctga tgtgggatcc  1200
tctgaccctc tgagcatggt gggaccttcc cagaacagaa gccccagcta cgcttcc     1257

SEQ ID NO: 52          moltype = DNA  length = 1257
FEATURE                Location/Qualifiers
CDS                    1..1257
                       note = nucleic acid molecule coding for DFD9
source                 1..1257
                       mol_type = other DNA
                       organism = synthetic construct
SEQUENCE: 52
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tgtacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
ctgggcaaag gcgggggagg cagcggggga ggcgggtccg gaggcggggg atctcatccc  720
atccctgact ccagtcctct cctgcaattc gggggccaag tccggcagcg gtacctctac  780
acagatgatg ctcagcagac agaagcccac ctggagatca gggaggatgg gaccgtgggg  840
ggcgctgctg accagagccc cgaaagtctc ctgcagctga aagccttgaa gcctggagtt  900
attcaaatct tgggagtcaa gactagtagg ttcctgtgcc agcggccaga tggggccctg  960
tatggatctc tccattttga ccctgaggcc tgcagcttcc gggagctgct tcttgaggac  1020
ggatacaatg tttaccagtc cgaagcccac ggcctccctc tgcatctgcc cgggaacaag  1080
tctcctcacc gggaccctgc ccccagagga cctgctcgct tcctgccact cccaggcctg  1140
ccccccgcat tgcctgagcc acccggaatc ctggcccccc agccccctga tgtgggatcc  1200
tctgaccctc tgagcatggt gggaccttcc cagggcagaa gccccagcta cgcttcc     1257

SEQ ID NO: 53          moltype = DNA  length = 1260
FEATURE                Location/Qualifiers
CDS                    1..1260
                       note = nucleic acid molecule coding for DFD13
source                 1..1260
                       mol_type = other DNA
                       organism = synthetic construct
SEQUENCE: 53
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tgtacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
```

```
ctgggcaaag gcgggggagg cagcggggga ggcgggtccg gaggcggggg atctcatccc  720
atccctgact ccagtcctct cctgcaattc gggggccaag tccggcagcg gtacctctac  780
acagatgatg ctcagcagac agaagcccac ctggagatca gggaggatgg gaccgtgggg  840
ggcgctgctg accagagccc cgaaagtctc ctgcagctga aagccttgaa gcctggagtt  900
attcaaatct tgggagtcaa gactagtagg ttcctgtgcc agcggccaga tggggccctg  960
tatggatctc tccattttga ccctgaggcc tgcagcttcc gggaggagat cagacccgac  1020
ggatacaatg tttaccagtc cgaagcccac ggcctccctc tgcatctgcc cgggaacaag  1080
tctcctcacc gggaccctgc cccagagga cctgctcgct tcctgccact cccaggcctg  1140
ccccccgcat tgcctgagcc acccggaatc ctggcccccc agccccctga tgtgggatcc  1200
tctgaccctc tgagcatggt gacaggcctg gaggccgtga gaagccccag ctacgcttcc  1260
```

```
SEQ ID NO: 54          moltype = DNA  length = 1260
FEATURE                Location/Qualifiers
CDS                    1..1260
                       note = nucleic acid molecule coding for DFD18
source                 1..1260
                       mol_type = other DNA
                       organism = synthetic construct
SEQUENCE: 54
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tgtacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
ctgggcaaag gcgggggagg cagcggggga ggcgggtccg gaggcggggg atctcatccc  720
atccctgact ccagtcctct cctgcaattc gggggccaag tccggcagcg gtacctctac  780
acagatgatg ctcagcagac agaagcccac ctggagatca gggaggatgg gaccgtgggg  840
ggcgctgctg accagagccc cgaaagtctc ctgcagctga aagccttgaa gcctggagtt  900
attcaaatct tgggagtcaa gactagtagg ttcctgtgcc agcggccaga tggggccctg  960
tatggatctc tccattttga ccctgaggcc tgcagcttcc gggaggagat cagacccgac  1020
ggatacaatg tttaccagtc cgaagcccac ggcctccctc tgcatctgcc cgggaacaag  1080
tctcctcacc gggaccctgc cccagagga cctgctcgct tcctgccact cccaggcctg  1140
ccccccgcat tgcctgagcc acccggaatc ctggcccccc agccccctga tgtgggatcc  1200
tctgaccctc tgagcatggt gacaggcctg gaggccgtga gaagccccag ctacgagtcc  1260
```

```
SEQ ID NO: 55          moltype = DNA  length = 1260
FEATURE                Location/Qualifiers
CDS                    1..1260
                       note = nucleic acid molecule coding for DFD72
source                 1..1260
                       mol_type = other DNA
                       organism = synthetic construct
SEQUENCE: 55
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tgtacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
ctgggcaaag gcgggggagg cagcggggga ggcgggtccg gaggcggggg atctcatccc  720
atccctgact ccagtcctct cctgcaattc gggggccaag tccggcagcg gtacctctac  780
acagatgatg ctcagcagac agaagcccac ctggagatca gggaggatgg gaccgtgggg  840
ggcgctgctg accagagccc cgaaagtctc ctgcagctga aagccttgaa gcctggagtt  900
attcaaatct tgggagtcaa gactagtagg ttcctgtgcc agcggccaga tggggccctg  960
tatggatctc tccattttga ccctgaggcc tgcagcttcc gggaggagat cagacccgac  1020
ggatacaatg tttaccagtc cgaagcccac ggcctccctc tgcatctgcc cgggaacaag  1080
tctcctcacc gggaccctgc cccagagga cctgctcgct tcctgccact cccaggcctg  1140
ccccccgcat tgcctgagcc acccggaatc ctggcccccc agccccctga tgtgggatcc  1200
tctgaccctc tgagcatggt gacaggcctg gaggccaaca gaagccccag ctacgagtcc  1260
```

```
SEQ ID NO: 56          moltype = DNA  length = 1257
FEATURE                Location/Qualifiers
CDS                    1..1257
                       note = nucleic acid molecule coding for DFD73
source                 1..1257
                       mol_type = other DNA
                       organism = synthetic construct
SEQUENCE: 56
```

-continued

```
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tgtacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
ctgggcaaag gcgggggagg cagcggggga ggcgggtccg gaggcggggg atctcatccc  720
atccctgact ccagtcctct cctgcaattc gggggccaag tccggcagcg gtacctctac  780
acagatgatg ctcagcagac agaagcccac ctggagatca gggaggatgg gaccgtgggg  840
ggcgctgctg accagagccc cgaaagtctc ctgcagctga aagccttgaa gcctggagtt  900
attcaaatct tgggagtcaa gactagtagg ttcctgtgcc agcggccaga tggggccctg  960
tatggatctc tccattttga ccctgaggcc tgcagcttcc gggaggagat cagacccgac  1020
ggatacaatg tttaccagtc cgaagcccac ggcctccctc tgcatctgcc cgggaacaag  1080
tctcctcacc gggaccctgc ccccagagga cctgctcgct tcctgccact cccaggcctg  1140
ccccccgcat tgcctgagcc acccggaatc ctggcccccc agccccctga tgtgggatcc  1200
tctgaccctc tgagcatggt gaacccttcc cagggcagaa gccccagcta cgcttcc     1257

SEQ ID NO: 57          moltype = DNA  length = 1257
FEATURE                Location/Qualifiers
CDS                    1..1257
                       note = nucleic acid molecule coding for DFD74
source                 1..1257
                       mol_type = other DNA
                       organism = synthetic construct
SEQUENCE: 57
gagaccaaga cacctgaatg tccaagtcac actcagcctc tgggagtgtt tctcttccca  60
cctaagccca aggataccct tatgatttct aggacacctg aggtgacctg cgtcgttgtg  120
gacgtgagtc aagaggaccc agaggtccag tttaactggt atgttgacgg cgtggaagtg  180
cataatgcaa aaactaaacc ccgcgaggaa caattcaatt caacctaccg ggtcgtttct  240
gtgttgacag tgctgcatca agattggctg aacgggaagg agtataagtg taaagtcagt  300
aataagggac tcccctctag tatcgaaaaa actatttcaa aggccaaagg ccagcctaga  360
gagccacagg tgtacaccct tcctccatcc caagaggaga tgacaaagaa ccaggtgtct  420
ctgacttgtc tcgtgaaggg gttctaccct agtgacatcg ctgtcgaatg ggagtcaaac  480
ggacagccag agaataatta taagacaact cctcccgttc tggattctga cggcagcttc  540
tttctgtact ctaggcttac tgtggacaaa agtcgctggc aagaagggaa cgtcttttca  600
tgttctgtta tgcacgaggc cttgcacaat cattatacac agaagtctct gagtctctca  660
ctgggcaaag gcgggggagg cagcggggga ggcgggtccg gaggcggggg atctcatccc  720
atccctgact ccagtcctct cctgcaattc gggggccaag tccggcagcg gtacctctac  780
acagatgatg ctcagcagac agaagcccac ctggagatca gggaggatgg gaccgtgggg  840
ggcgctgctg accagagccc cgaaagtctc ctgcagctga aagccttgaa gcctggagtt  900
attcaaatct tgggagtcaa gactagtagg ttcctgtgcc agcggccaga tggggccctg  960
tatggatctc tccattttga ccctgaggcc tgcagcttcc gggaggagat cagacccgac  1020
ggatacaatg tttaccagtc cgaagcccac ggcctccctc tgcatctgcc cgggaacaag  1080
tctcctcacc gggaccctgc ccccagagga cctgctcgct tcctgccact cccaggcctg  1140
ccccccgcat tgcctgagcc acccggaatc ctggcccccc agccccctga tgtgggatcc  1200
tctgaccctc tgagcatggt gaacccttcc cagggcagaa gccccagcta cgagtcc     1257
```

USE OF LONG-ACTING FGF21 FUSION PROTEINS IN TREATING FGF21-ASSOCIATED DISORDERS

CROSS REFERENCE TO RELATED APPLICATIONS

This application is a Continuation of U.S. application Ser. No. 17/478,600 filed Sep. 17, 2021, which is a Divisional of U.S. application Ser. No. 15/768,616 filed Apr. 16, 2018, now U.S. Pat. No. 11,142,557 issued Oct. 12, 2021, which is a National Stage of International Application No. PCT/KR2016/012288 filed Oct. 28, 2016, claiming priority based on Korean Patent Application No. 10-2015-0150574 filed Oct. 28, 2015.

SEQUENCE LISTING

The content of the electronically submitted sequence listing, file name: Q292897SEQLISTST26ASFILED.XML; size: 99,000 bytes; and date of creation: Oct. 19, 2023, filed herewith, is incorporated herein by reference in its entirety.

TECHNICAL FIELD

The present invention relates to a fusion protein comprising a fibroblast growth factor 21 (FGF21) mutant protein with improved in vivo duration, protein stability and pharmacological activity, and a pharmaceutical composition comprising the same.

BACKGROUND ART

Fibroblast growth factor 21 (FGF21), synthesized in the liver, is a hormone known to play an important role in glucose and lipid homeostasis. FGF21 exhibits pharmacological actions in the liver, adipocytes, B cells of the pancreas, hypothalamus in the brain, and muscle tissues, where both an FGF21-specific receptor, i.e., FGF receptor, and β-klotho complex are expressed. It has been reported that in non-human primate and murine models of various diabetic and metabolic diseases, FGF21 can lower blood glucose levels in an insulin-independent manner, reduce body weight, and lower triglyceride and low-density lipoprotein (LDL) concentrations in the blood. Additionally, due to its effect of improving insulin sensitivity, FGF21 has potential for development as a novel therapeutic agent for diabetes and obesity (see WO2003/011213).

Accordingly, in order to develop a novel anti-diabetic drug based on FGF21, attempts have been made to improve its biological activity and in vivo stability by constructing FGF21 mutants based on the wild-type FGF21 sequence via substitution, insertion, and deletion of some amino acids (see WO2010/065439). However, as FGF21 has a very short half-life, it has proven problematic if used directly as a biotherapeutic agent (Kharitonenkov, A. et al. (2005) Journal of Clinical Investigation 115:1627-1635). The in vivo half-life of FGF21 is 1 to 2 hours in mice, and 2.5 to 3 hours in monkeys. Therefore, for FGF21 to be used in its current form as a therapeutic agent for diabetes, daily administration is required.

Various approaches have been reported in attempting to increase the in vivo half-life of FGF21 recombinant proteins. One such example is to link polyethylene glycol (PEG), i.e., a polymer material, to FGF21 to increase its molecular weight, thereby inhibiting renal excretion and increasing in vivo retention time (see WO2012/066075). Another approach attempts to improve the half-life by fusing it with a fatty acid, which binds to human albumin (see WO2012/010553). An additional example attempts to increase the half-life while maintaining pharmacological activity equivalent to that of wild-type FGF21 through the generation of an agonist antibody, which specifically binds to the human FGF receptor alone or as a complex with β-klotho (see WO2012/170438). In another example, the half-life was improved by preparing long-acting fusion proteins, in which an Fc region of IgG is fused to an FGF21 molecule (see WO2013/188181).

Among the various technologies available to create long-acting drugs, Fc fusion technology is widely used because it has less of the disadvantages seen with other approaches, such as inducing an immune response or toxicity while increasing in vivo half-life. For the development of an Fc-fused FGF21 protein as a long-acting therapeutic drug, the following conditions should be satisfied.

First, the decrease of in vitro activity caused by fusion should be minimized. Both the N-terminus and C-terminus of FGF21 are involved in FGF21's activity. In this regard, it is known that the activities of FGF21 fusion proteins greatly vary depending on the location of the fusion. Accordingly, the activities of Fc-fused FGF21 fusion proteins, in which mutations are introduced into FGF21, may be altered depending on the presence/absence or location of the fusion. Second, a pharmacokinetic profile enabling administration at an interval of once per week in humans should be realized by the increase of in vivo half-life by the fusion. Third, considering that immunogenicity may be expected in most patients after administration of biopharmaceuticals, the immunogenicity risk due to a fusion linker or mutation should be minimized. Fourth, there should be no stability issues arising from the position of the fusion or the introduction of the mutation. Fifth, since undesired immune responses may occur depending on the isotypes of fused immunoglobulin, a solution to prevent such responses is necessary.

An attempt to develop a long-acting fusion protein by linking the Fc region of an immunoglobulin G (IgG) to an FGF21 molecule has already been reported (see WO 2013/188181). In the case of one Fc-FGF21 structure, where the Fc is fused to the N-terminus of the wild-type FGF21, while there is no distinct difference in in vitro activity as compared to that of the wild-type FGF21, the half-life is known to be very short due to in vivo degradation of the protein. To address this issue, there has been an attempt to improve the in vivo half-life by introducing several mutations at specific site locations of FGF21 to resist protein degradation. However, immunogenicity risk may increase with the introduction of multiple mutations. In contrast, in the case of an FGF21-Fc structure, where the Fc is fused to the C-terminus of the FGF21 molecule, it is known that there is a significant decrease in activity caused by fusion at this site when compared to the Fc-FGF21 structure.

The present inventors have endeavored to improve the physiological activity and stability of FGF21 and discovered that the pharmacological efficacy of FGF21 may be improved and the in vivo exposure and half-life of FGF21 may be increased without compromising the in vitro activity when a mutation is introduced into a particular location of FGF21 and the immunoglobulin Fc region is linked thereto, thereby accomplishing the present invention.

DISCLOSURE OF INVENTION

Technical Problem

An object of the present invention is to provide a fusion protein comprising an FGF21 mutant protein with improved in vivo duration, protein stability and pharmacological efficacy.

Another object of the present invention is to provide a pharmaceutical composition comprising the fusion protein.

A further object of the present invention is to provide an isolated nucleic acid molecule encoding the fusion protein, an expression vector comprising the nucleic acid molecule, and a host cell comprising the expression vector.

Solution to Problem

The present invention provides a fusion protein comprising an FGF21 mutant protein and an Fc region of an immunoglobulin, wherein the FGF21 mutant protein comprises at least one mutation selected from the group consisting of the following mutations (1) to (7):

(1) a substitution of amino acids at positions 98 to 101 from the N-terminus of a wild-type FGF21 protein with an amino acid sequence of EIRP (SEQ ID NO: 42);

(2) a substitution of amino acids at positions 170 to 174 from the N-terminus of a wild-type FGF21 protein with an amino acid sequence of TGLEAV (SEQ ID NO: 43);

(3) a substitution of amino acids at positions 170 to 174 from the N-terminus of a wild-type FGF21 protein with an amino acid sequence of TGLEAN (SEQ ID NO: 44);

(4) a substitution of an amino acid at position 170 from the N-terminus of a wild-type FGF21 protein with an amino acid N;

(5) a substitution of an amino acid at position 174 from the N-terminus of a wild-type FGF21 protein with an amino acid N;

(6) a substitution of an amino acid at position 180 from the N-terminus of a wild-type FGF21 protein with an amino acid E, along with one or more mutations (1) to (5) above; and (7) a mutation of 1 to 10 amino acids for reducing immunogenicity of a wild-type FGF21 protein.

In addition, the present invention provides a pharmaceutical composition comprising a fusion protein for treating diabetes, obesity, dyslipidemia, metabolic syndrome, non-alcoholic fatty liver disease or non-alcoholic steatohepatitis.

Further, the present invention provides an isolated nucleic acid molecule encoding the fusion protein, an expression vector comprising the nucleic acid molecule, and a host cell comprising the expression vector.

Advantageous Effects of Invention

The fusion protein of the present invention, prepared by linking an Fc region of a human immunoglobulin to an FGF21 mutant protein, has improved in vivo duration, protein stability and pharmacological efficacy. In addition, a pharmaceutical composition comprising the fusion protein as an active ingredient can be used as a therapeutic agent for diabetes, obesity, dyslipidemia, metabolic syndrome, non-alcoholic fatty liver disease or non-alcoholic steatohepatitis. In particular, the pharmaceutical composition of the present invention has the advantage of a long administration interval due to increased in vivo stability of the FGF21 fusion protein compared with that of the conventional pharmaceutical composition comprising an FGF21 protein.

BEST MODE FOR CARRYING OUT THE INVENTION

Figure 1A:
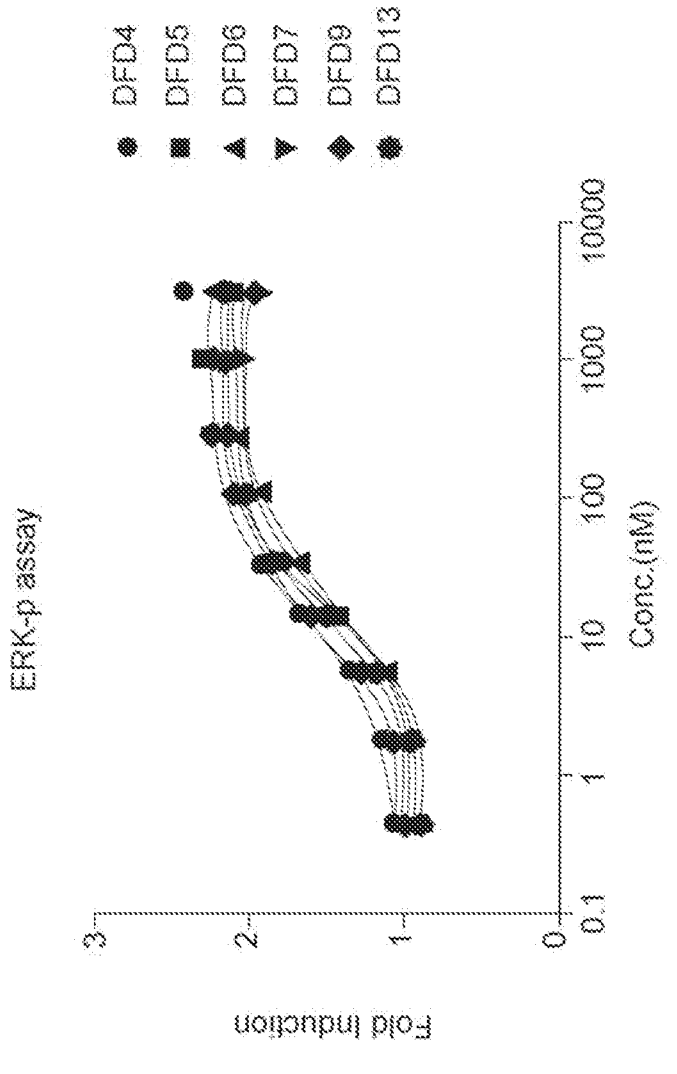
FIGS. 1A to 1C are graphs showing the measurement results of in vitro activities of fusion proteins including FGF21 mutant proteins (hereinafter, "FGF21 mutant fusion protein") by using a HEK293 cell line in which human β-klotho is overexpressed. No FGF21 mutant fusion protein variants showed a significant decrease in activity due to the introduction of mutations.

Hereinafter, the present invention will be described in more detail.

In an aspect, the present invention provides a fusion protein comprising a fibroblast growth factor 21 (FGF21) mutant protein and an Fc region of an immunoglobulin, wherein the FGF21 mutant protein comprises at least one mutation selected from the group consisting of the following mutations (1) to (7):

(1) a substitution of amino acids at positions 98 to 101 from the N-terminus of a wild-type FGF21 protein with an amino acid sequence of EIRP (SEQ ID NO: 42) (hereinafter, "EIRP");

(2) a substitution of amino acids at positions 170 to 174 from the N-terminus of a wild-type FGF21 protein with an amino acid sequence of TGLEAV (SEQ ID NO: 43) (hereinafter, "TGLEAV");

(3) a substitution of amino acids at positions 170 to 174 from the N-terminus of a wild-type FGF21 protein with an amino acid sequence of TGLEAN (SEQ ID NO: 44) (hereinafter, "TGLEAN");

(4) a substitution of an amino acid at position 170 from the N-terminus of a wild-type FGF21 protein with an amino acid N (hereinafter, "G170N");

(5) a substitution of an amino acid at position 174 from the N-terminus of a wild-type FGF21 protein with an amino acid N (hereinafter, "G174N");

(6) a substitution of an amino acid at position 180 from the N-terminus of a wild-type FGF21 protein with an amino acid E (hereinafter, "A180E"), along with one or more mutations (1) to (5) above; and (7) a mutation of 1 to 10 amino acids for reducing immunogenicity of a wild-type FGF21 protein.

The wild-type FGF21 protein, a hormone known to play an important role in glucose and lipid homeostasis, may be one derived from mammals such as humans, mice, pigs, monkeys, etc., preferably from humans. More preferably, the wild-type FGF21 protein may be the wild-type human FGF21 protein having an amino acid sequence represented by SEQ ID NO: 1.

The mutation included in the FGF21 mutant proteins may be, preferably, any one of the mutations of EIRP (SEQ ID NO: 42), TGLEAV (SEQ ID NO: 43), TGLEAN (SEQ ID NO: 44), G170N and G174N; a combination of any one of the mutations of TGLEAV (SEQ ID NO: 43), TGLEAN (SEQ ID NO: 44), G170N and G174N and the mutation of EIRP (SEQ ID NO: 42); a combination of any one of the mutations of EIRP (SEQ ID NO: 42), TGLEAV (SEQ ID NO: 43), TGLEAN (SEQ ID NO: 44), G170N and G174N and the mutation of A180E; or a combination of any one of the mutations of TGLEAV (SEQ ID NO: 43), TGLEAN (SEQ ID NO: 44), G170N and G174N, the mutation of EIRP (SEQ ID NO: 42) and the mutation of A180E. Furthermore, the FGF21 mutant proteins may have a conformation, in which 1 to 10 amino acids at the N-terminus or C-terminus is (are) deleted as compared to the wild-type FGF21 protein. More preferably, the FGF21 mutant proteins may include an amino acid sequence represented by any one of SEQ ID NO: 6 to 23. Still more preferably, the FGF21 mutant proteins may include an amino acid sequence represented by any one of SEQ ID NO: 6 to 23 and further have a conformation, in which 1 to 10 amino acids at the N-terminus or C-terminus is (are) deleted as compared to the wild-type FGF21 protein.

In the fusion protein, an amino acid residue N of FGF21 mutant protein introduced by a mutation may be glycosylated.

As used herein, the term "Fc region," "Fc fragment," or "Fc" refers to a protein, which includes a heavy chain constant region 1 (CH1), a heavy chain constant region 2 (CH2) and a heavy chain constant region 3 (CH3) of an immunoglobulin, but does not include variable regions of the heavy and light chains and a light chain constant region 1 (CL1) of an immunoglobulin. Additionally, as used herein, the term "Fc region mutant" refers to one prepared by substituting part of amino acid(s) of an Fc region or by combining Fc regions of different types.

The Fc region of immunoglobulin may be an entire Fc region constituting an antibody, a fragment thereof, or an Fc region mutant. Additionally, the Fc region includes a molecule in the form of a monomer or multimer, and may further include a hinge region of the heavy chain constant region. The Fc region mutant may be modified to prevent cleavage at the hinge region. Furthermore, the hinge sequence of the Fc may have a substitution in some amino acid sequences to reduce antibody-dependent cell-mediated cytotoxicity (ADCC) or complement-dependent cytotoxicity (CDC). In addition, part of the amino acid sequence of the Fc hinge sequence may be substituted to inhibit the rearrangement of the Fab region. A lysine residue at the C-terminus of the Fc may be removed.

Preferably, the Fc region of immunoglobulin may be any one of IgG1, IgG2, IgG3, IgG4 and IgD Fc regions; or a hybrid Fc, which is a combination thereof. Further, the hybrid Fc may include an IgG4 region and an IgD region. Further, the hybrid Fc region may include part of the hinge sequence and CH2 of an IgD Fc, and CH2 and CH3 sequences of IgG4 Fc.

In addition, the Fc fragment of the present invention may be in the form of wild-type glycosylated chain, more glycosylated chain than the wild-type, less glycosylated chain than the wild-type, or deglycosylated chain. The increase, decrease, or removal of glycosylated chain may be performed by a conventional method known in the art, such as a chemical method, an enzymatic method, and a genetic engineering method using microorganisms.

Further, the immunoglobulin Fc region may be represented by SEQ ID NO: 24 or 25. In addition, the immunoglobulin Fc region may be represented by SEQ ID NO: 26.

Additionally, the fusion protein may further comprise a linker.

The fusion protein may be in the form, in which the FGF21 mutant protein is directly connected to the N-terminus or C-terminus of the immunoglobulin Fc region, or the FGF21 mutant protein is connected to the immunoglobulin Fc region via a linker.

In such case, the linker may be connected to the N-terminus, C-terminus, or a free radical of the Fc fragment, and also, may be connected to the N-terminus, C-terminus, or a free radical of the FGF21 mutant protein. When the linker is a peptide linker, the connection may occur in any region. For example, the linker may be connected to the C-terminus of the immunoglobulin Fc region and the N-terminus of the FGF21 mutant protein to form a fusion protein of the immunoglobulin Fc region and the FGF21 mutant protein.

When the linker and Fc are separately expressed and then connected, the linker may be a crosslinking agent known in the art. Examples of the crosslinking agent may include 1,1-bis(diazoacetyl)-2-phenylethane, glutaraldehyde, imidoesters including N-hydroxysuccinimide ester such as 4-azidosalicylic acid and disuccinimidyl esters such as 3,3'-dithiobis(succinimidylpropionate), and bifunctional maleimides such as bis-N-maleimido-1,8-octane, but are not limited thereto.

Further, the linker may be a peptide. Preferably, the linker may be a peptide consisting of 10 to 30 amino acid residues.

Furthermore, alanine may additionally be attached to the end of the linker. Preferably, the linker may be a peptide having an amino acid sequence represented by any one of SEQ ID NO: 2 to 5.

The fusion protein may be in a form in which a dimer or a multimer of FGF21 mutant proteins, in which one or more FGF21 mutant proteins linked together, is connected to an immunoglobulin Fc region. Additionally, the fusion protein may be in a form of a dimer or multimer in which two or more immunoglobulin Fc regions are linked, wherein the immunoglobulin Fc regions have the FGF21 mutant protein connected thereto.

Additionally, the fusion protein may be a peptide which preferably has an amino acid sequence represented by any one of SEQ ID NO: 27 to 39. More preferably, the fusion protein including the FGF21 mutant protein may be a peptide which has an amino acid sequence represented by SEQ ID NO: 36, 37 or 39.

The immunogenicity as described in the above (7) may be predicted by a conventional method known in the art. For example, the potential immunogenicity of a protein may be screened by using, e.g., ITOPE™ and TCED™ methods.

Further, the mutations for minimizing the immunogenicity may be designed by a conventional method known in the art. For example, when immunogenicity is observed by performing an EPISCREEN™ analysis to evaluate potential immunogenicity, the amino acid sequences inducing the immunogenicity may be identified through T-cell epitope mapping, and the mutants with minimized immunogenicity may be designed via in silico prediction.

The fusion protein may have a form with which one or more biologically active proteins is (are) further coupled. The biologically active protein may be one selected from the group consisting of insulin, C-peptide, leptin, glucagon, gastrin, gastric inhibitory polypeptide (GIP), amylin, calcitonin, cholecystokinin, peptide YY, neuropeptide Y, bone morphogenetic protein-6 (BMP-6), bone morphogenetic protein-9 (BMP-9), oxyntomodulin, oxytocin, glucagon-like peptide-1 (GLP-1), glucagon-like peptide-2 (GLP-2), irisin, fibronectin type III domain-containing protein 5 (FNDC5), apelin, adiponectin, C1q and tumor necrosis factor related protein (CTRP family), resistin, visfatin, omentin, retinol binding protein-4 (RBP-4), glicentin, angiopoietin, interleukin-22 (IL-22), exendin-4 and growth hormone. Preferably, the biologically active protein may be one selected from GLP-1, a mutant thereof and exendin-4.

In another aspect, the present invention provides a pharmaceutical composition containing the fusion protein for treating FGF21-associated disorders.

As used herein, the term "FGF21-associated disorder" may include obesity, type I- and type II diabetes, pancreatitis, dyslipidemia, non-alcoholic fatty liver disease (NAFLD), non-alcoholic steatohepatitis (NASH), insulin resistance, hyperinsulinemia, glucose intolerance, hyperglycemia, metabolic syndrome, acute myocardial infarction, hypertension, cardiovascular diseases, atherosclerosis, peripheral arterial disease, apoplexy, heart failure, coronary artery heart disease, renal disease, diabetic complications, neuropathy, gastroparesis, disorder associated with a serious inactivation mutation in insulin receptor, and other metabolic disorders. Preferably, the FGF21-associated disorder may be diabetes, obesity, dyslipidemia, metabolic syndrome, non-alcoholic fatty liver disease, non-alcoholic steatohepatitis or cardiovascular diseases.

Further, the pharmaceutical composition may further include a pharmaceutical carrier. The pharmaceutical carrier may be any carrier as long as it is a non-toxic material suitable for delivering antibodies to patients. For example, distilled water, alcohol, fats, waxes and inactive solids may be included as a carrier. Pharmaceutically acceptable adjuvants (buffering agents, dispersants) may also be included in the pharmaceutical composition. In these formulations, the concentration of the fusion protein may vary greatly.

Specifically, the pharmaceutical composition may contain a formulation material for altering, maintaining, or conserving the pH, osmolarity, viscosity, transparency, color, isotonicity, odor, sterility, stability, dissolution or release rate, adsorption, or permeability of the composition. Examples of the suitable formulating material may include amino acids (e.g., glycine, glutamine, asparagine, arginine or lysine), anti-microorganism agents, anti-oxidants (e.g., ascorbic acid, sodium sulfite or sodium bisulfite), buffering agents (e.g., borate, bicarbonates, Tris-HCl, citrate, phosphate or other organic acids), bulking agents (e.g., mannitol or glycine), chelating agents (e.g., ethyelenediaminetetraacetic acid (EDTA)), complexing agents (e.g., caffeine, polyvinylpyrrolidione, β-cyclodextrin or hydroxypropyl-β-cyclodextrin), fillers, monosaccharides, disaccharides and other carbohydrates (e.g., glucose, mannose or dextrin), proteins (e.g., serum albumin, gelatin or immunoglobulin), coloring agents, flavoring agents, diluents, emulsifiers, hydrophilic polymers (e.g., polyvinylpyrrolidione), low molecular weight polypeptides, salt-forming counterions (e.g., sodium), preservatives (e.g., benzalkonium chloride, benzoic acid, salicylic acid, thimerosal, phenethyl alcohol, methylparaben, propylparaben, chlorhexidine, sorbic acid or hydrogen peroxide), solvents (e.g., glycerin, propylene glycol or polyethylene glycol), sugar alcohols (e.g., mannitol or sorbitol), suspending agents, surfactants or humectants (e.g., pluronics; PEG; sorbitan ester; polysorbate, e.g., polysorbate 20 or polysorbate 80; triton; tromethamine; lecithin; cholesterol or tyloxapol), stability improvers (e.g., sucrose or sorbitol), growth improvers (e.g., alkali metal halides, preferably, sodium chloride or potassium chloride; or mannitol, sorbitol), delivery vehicles, diluents, excipients and/or pharmaceutical adjuvants, but are not limited thereto.

In another aspect, the present invention provides a method for preventing or treating FGF21-associated disorders including administering the fusion protein to a subject in need of such prevention or treatment. This method includes, in particular, administering an effective amount of the fusion protein of the present invention to a mammal having a symptom of diabetes, obesity, dyslipidemia, metabolic syndrome, non-alcoholic fatty liver disease, non-alcoholic steatohepatitis or cardiovascular diseases which are FGF21-associated disorders.

The pharmaceutical composition of the present invention may be administered via any route. The composition of the present invention may be provided to an animal directly (e.g., topically, by administering into tissue areas by injection, transplantation, or by topical administration) or systemically (e.g., by oral- or parenteral administration) via any appropriate means. When the composition of the present invention is parenterally provided via intravenous-, subcutaneous-, ophthalmic-, intraperitoneal-, intramuscular-, oral-, rectal-, intraorbital-, intracerebral-, intracranial-, intraspinal-, intraventricular-, intrathecal-, intracistenal-, intracapsular-, intranasal-, or aerosol administration, the composition is preferably aqueous or may include a portion of a physiologically applicable body liquid suspension or solution. Accordingly, the carrier or vehicle may be added to the composition and be delivered to a patient since it is physiologically applicable. Therefore, a physiologically-appropriate saline solution may generally be included as a carrier like a body fluid for formulations.

Further, the administration frequency may vary depending on the pharmacokinetic parameters of the fusion protein in the formulations to be used. Typically, physicians would administer the composition until an administration dose to achieve a desired effect is reached. Accordingly, the composition may be administered as a unit dose, at least two doses with time intervals (may or may not contain the same amount of a target fusion protein) or administered by a continuous injection via a transplantation device or catheter. The precision of addition of an appropriate administration dose may be routinely performed by those skilled in the art, and corresponds to the scope of work being routinely performed by them.

Additionally, the preferable unit dose of the fusion protein in humans may be in a range from 0.01 μg/kg to 100 mg/kg of body weight, and more preferably from 1 μg/kg to 10 mg/kg of body weight. Although this is the optimal amount, the unit dose may vary depending on the disease to be treated or the presence/absence of adverse effects. Nevertheless, the optimal administration dose may be determined by performing a conventional experiment. The administration of the fusion protein may be performed by a periodic bolus injection, an external reservoir (e.g., an intravenous bag), or a continuous intravenous-, subcutaneous-, or intraperitoneal administration from the internal source (e.g., a bioerodible implant).

In addition, the fusion protein of the present invention may be administered to a subject recipient along with other biologically active molecules. The optimal combination of the fusion protein and other molecule(s), dosage forms, and optimal doses may be determined by a conventional experiment well known in the art.

In still another aspect, the present invention provides an isolated nucleic acid molecule encoding the fusion protein.

As used herein, the term "isolated nucleic acid molecule" refers to a nucleic acid molecule of the present invention, which is isolated from about at least 50% of proteins, lipids, carbohydrates, or other materials, discovered in nature when total nucleic acids are isolated from a source cell; which is operatively linked to a polynucleotide which is not linked in nature; or which is a part of a larger polynucleotide sequence and does not occur in nature. Preferably, in the isolated nucleic acid molecules of the present invention, there are not substantially present any other contaminated nucleic acids, or other contaminants which are discovered in the natural environment and inhibit uses of the nucleic acids in the production of polypeptides, or treatment, diagnosis, prevention, or research.

In such case, the isolated nucleic acid molecules encoding the fusion protein may have different sequences with each other due to codon redundancy. Furthermore, as long as the isolated nucleic acid can produce the fusion protein, the isolated nucleic acid may be appropriately modified, or a nucleotide may be added to the N-terminus or C-terminus of the isolated nucleic acid according to desired purposes.

The isolated nucleic acid may include, for example, a nucleotide sequence represented by any one of SEQ ID NO: 45 to 57.

In still another aspect, the present invention provides an expression vector comprising the isolated nucleic acid molecule, which encodes the fusion protein including an FGF21 mutant protein and an Fc region of an immunoglobulin.

As used herein, the term "expression vector" refers to a vector containing a nucleic acid sequence, which is suitable for the transformation of a host cell and directs or controls the expression of an inserted heterogenous nucleic acid sequence. The expression vector includes a linear nucleic acid, a plasmid, a phagemid, a cosmid, an RNA vector, a viral vector, and analogs thereof. Examples of the viral vector include a retrovirus, an adenovirus and an adeno-associated virus, but are not limited thereto.

As used herein, the term "expression of a heterogeneous nucleic acid sequence" or "expression" of a target protein refers to transcription of an inserted DNA sequence, translation of an mRNA transcript, and production of an Fc fusion protein product, an antibody or an antibody fragment.

A useful expression vector may be RcCMV (Invitrogen, Carlsbad) or a mutant thereof. The useful expression vector may include a human cytomegalovirus (CMV) promoter for promoting a continuous transcription of a target gene in a mammalian cell, and a bovine growth hormone polyadenylation signal sequence for enhancing the level of post-transcriptional RNA stability. In an exemplary embodiment of the present invention, the expression vector is pAD15, which is a modified vector of RcCMV.

In still another aspect, the present invention provides a host cell comprising the expression vector.

As used herein, the term "host cell" refers to a prokaryotic cell or eukaryotic cell into which a recombinant expression vector may be introduced. As used herein, the term "transformed" or "transfected" refers to introduction of a nucleic acid (e.g., a vector) into a cell by various technologies known in the art.

An appropriate host cell may be transformed or transfected with a DNA sequence of the present invention and may be used for the expression and/or secretion of the target protein. Examples of the appropriate host cell that may be used in the present invention include immortal hybridoma cells, NS/0 myeloma cells, 293 cells, Chinese hamster ovary (CHO) cells, HeLa cells, CAP cells (human amniotic fluid-derived cells), and COS cells.

Hereinafter, exemplary embodiments of the present invention will be described in detail with reference to the examples. However, these examples according to the present invention can be modified in many different forms and the scope of the present invention should not be construed as limited to the examples set forth herein.

MODE FOR THE INVENTION

Preparation Example 1. Preparation and Purification of Fusion Protein Containing FGF21 Mutant Protein

Preparation Example 1-1. Preparation of Expression Vectors for Expression of FGF21 Mutant Proteins In order to improve the stability, activity and pharmacokinetic profiles of the FGF21 in an Fc-FGF21 structure, mutation studies of FGF21 were performed.

Specifically, mutant proteins were designed for the LLLE region (SEQ ID NO: 58) (the amino acids at positions 98 to 101 from the N-terminus of the FGF21 protein) and GPSQG region (SEQ ID NO: 59) (the amino acids at positions 170 to 174 from the N-terminus of the FGF21 protein), and A180 site, which were expected to significantly affect protein activities based on 3-dimensional structure analysis of the FGF21 proteins.

The position, sequence information, target and expected effect of each mutation introduced into the FGF21 protein are listed in Table 1 below (in Table 1, N refers to glycosylated asparagine (N)). Further, FGF21 mutant proteins including the mutations described in Table 1 are listed in Table 2 below.

TABLE 1

| Sequence | Position | Original sequence | Mutated sequence | Target | Expected effect |
|---|---|---|---|---|---|
| EIRP (SEQ ID NO: 42) | 98-101 | LLLE (SEQ ID NO: 58) | EIRP (SEQ ID NO: 42) | Substitution with FGF19 sequence | Improvement of stability and pharmacokinetics |
| TGLEAV (SEQ ID NO: 43) | 170-174 | GPSQG (SEQ ID NO: 59) | TGLEAV (SEQ ID NO: 43) | Substitution with FGF19 sequence | Improvement of pharmacokinetics |
| TGLEAN (SEQ ID NO: 44) | 170-174 | GPSQG (SEQ ID NO: 59) | TGLEA<u>N</u> (SEQ ID NO: 44) | Substitution with FGF19 sequence, and addition of N-glycosylation | Improvement of pharmacokinetics |
| G170N | 170 | G | <u>N</u> | Point mutation, and addition of N-glycosylation | Improvement of pharmacokinetics |
| G174N | 174 | G | <u>N</u> | Point mutation, and addition of N-glycosylation | Improvement of pharmacokinetics |
| A180E | 180 | A | E | Point mutation | Improvement of pharmacokinetics |

TABLE 2

| SEQ ID NO | Sequence of FGF21 mutant protein |
|---|---|
| 6 | FGF21 (EIRP (SEQ ID NO: 42)) |
| 7 | FGF21 (TGLEAV (SEQ ID NO: 43)) |
| 8 | FGF21 (TGLEAN (SEQ ID NO: 44)) |
| 9 | FGF21 (G170N) |
| 10 | FGF21 (G174N) |
| 11 | FGF21 (EIRP (SEQ ID NO: 42), TGLEAV (SEQ ID NO: 43)) |
| 12 | FGF21 (EIRP (SEQ ID NO: 42), TGLEAN (SEQ ID NO: 44)) |
| 13 | FGF21 (EIRP (SEQ ID NO: 42), G170N) |
| 14 | FGF21 (EIRP (SEQ ID NO: 42), G174N) |
| 15 | FGF21 (EIRP (SEQ ID NO: 42), A180E) |
| 16 | FGF21 (TGLEAV (SEQ ID NO: 43), A180E) |
| 17 | FGF21 (TGLEAN (SEQ ID NO: 44), A180E) |
| 18 | FGF21 (G170N, A180E) |
| 19 | FGF21 (G174N, A180E) |
| 20 | FGF21 (EIRP (SEQ ID NO: 42), TGLEAV (SEQ ID NO: 44), A180E) |
| 21 | FGF21 (EIRP (SEQ ID NO: 42), TGLEAN (SEQ ID NO: 44), A180E) |
| 22 | FGF21 (EIRP (SEQ ID NO: 42), G170N, A180E) |
| 23 | FGF21 (EIRP (SEQ ID NO: 42), G174N, A180E) |

Expression vectors were prepared to express the amino acids of the three components: fusion carrier, linker and FGF21 mutant in this order from the N-terminus to C-terminus. The material code of each FGF21 mutant fusion protein, sequence of mutation introduced into FGF21, sequence of fusion carrier and linker sequence are listed in Table 3 below 5 (in Table 3, N refers to glycosylated asparagine (N)).

TABLE 3

| SEQ ID NO | Material code | Sequence of FGF21 mutation | Fusion carrier | Linker sequence |
|---|---|---|---|---|
| 27 | DFD1 | EIRP (SEQ ID NO: 42), TGLEAV (SEQ ID NO: 43) | hyFc (SEQ ID NO: 26) | C (SEQ ID NO: 2) |
| 28 | DFD3 | TGLEAV (SEQ ID NO: 43) | hyFc (SEQ ID NO: 26) | AKA (SEQ ID NO: 3) |
| 29 | DFD4 | TGLEAV (SEQ ID NO: 43) | hyFc (SEQ ID NO: 26) | GS3 (SEQ ID NO: 4) |
| 30 | DFD5 | TGLEAN (SEQ ID NO: 44) | hyFc (SEQ ID NO: 26) | GS3 (SEQ ID NO: 4) |
| 31 | DFD6 | G170N | hyFc (SEQ ID NO: 26) | GS3 (SEQ ID NO: 4) |
| 32 | DFD6 (*E. coli*) | G170N | hyFc (SEQ ID NO: 26) | GS3 (SEQ ID NO: 4) |
| 33 | DFD7 | G174N | hyFc (SEQ ID NO: 26) | GS3 (SEQ ID NO: 4) |
| 34 | DFD9 | none | hyFc (SEQ ID NO: 26) | GS3 (SEQ ID NO: 4) |
| 35 | DFD13 | EIRP (SEQ ID NO: 42), TGLEAV (SEQ ID NO: 43) | hyFc (SEQ ID NO: 26) | GS3 (SEQ ID NO: 4) |
| 36 | DFD18 | EIRP (SEQ ID NO: 42), TGLEAV (SEQ ID NO: 43) A180E | hyFc (SEQ ID NO: 26) | GS3 (SEQ ID NO: 4) |
| 37 | DFD72 | EIRP (SEQ ID NO: 42), TGLEAN (SEQ ID NO: 44) A180E | hyFc (SEQ ID NO: 26) | GS3 (SEQ ID NO: 4) |
| 38 | DFD73 | EIRP (SEQ ID NO: 42), G170N | hyFc (SEQ ID NO: 26) | GS3 (SEQ ID NO: 4) |
| 39 | DFD74 | EIRP (SEQ ID NO: 42), G170N, A180E | hyFc (SEQ ID NO: 26) | GS3 (SEQ ID NO: 4) |

TABLE 3-continued

| SEQ ID NO | Material code | Sequence of FGF21 mutation | Fusion carrier | Linker sequence |
|---|---|---|---|---|
| 40 | RGE (Amgen) | L98R, P171G, A180E | IgG1Fc mutant | GS3 (SEQ ID NO: 4) |
| 41 | Fc-FGF21 (Lilly) | X | IgG4Fc mutant (SEQ ID NO: 25) | GS3A (SEQ ID NO: 5) |

In order to produce the FGF21 mutant fusion proteins, the nucleotide sequences encoding each of the FGF21 mutant proteins were synthesized by consulting with Bioneer Corporation (Korea) based on the amino acid sequence of each protein. NheI and NotI restriction enzyme sequences were added to the 5' terminus and 3' terminus of the nucleotide sequences encoding each of the FGF21 mutant proteins and an initiation codon for protein translation and a leader sequence (MDAMLRGLCCVLLLCGAVFVSPSHA) (SEQ ID NO: 60) capable of secreting the expressed protein to the outside of a cell were inserted next to the restriction enzyme sequence at the 5' terminus. A termination codon was inserted next to the nucleotide sequence, which encodes each of the FGF21 mutant fusion proteins. The nucleotide sequence encoding each of the FGF21 mutant fusion proteins was cloned into a pTrans-empty expression vector by using the two restriction enzymes of NheI and NotI. The pTrans-empty expression vector, which has a simple structure including a CMV promoter, a pUC-derived replication origin, an SV40-derived replication origin and an ampicillin-resistant gene, was purchased from CEVEC Pharmaceuticals (Germany).

In the case of the fusion proteins of DFD6 (*E. coli*) and RGE (Amgen), the nucleotide sequence encoding each fusion protein was inserted into a pET30a expression vector for expression in *E. coli.*

Preparation Example 1-2. Construction of Plasmid DNA for Expression of FGF21 Mutant Fusion Proteins

*E. coli* was transformed with each of the expression vectors constructed in Preparation Example 1-1 to obtain a large amount of plasmid DNA to be used for expression. *E. coli* cells, whose cell walls were weakened, were transformed with each expression vector through heat shock, and the transformants were plated out on LB plates to obtain colonies. The colonies thus obtained were inoculated into LB media, cultured at 37° C. for 16 hours, and each *E. coli* culture containing each expression vector was obtained in a volume of 100 mL. The *E. coli* thus obtained was centrifuged to remove the culture medium, and then P1, P2, P3 solutions (QIAGEN, Cat No.: 12963) were added to break the cell walls, thereby obtaining a DNA suspension in which proteins and DNAs were separated. Plasmid DNA was purified from the DNA suspension thus obtained by using a QIAGEN™ DNA purification column. The eluted plasmid DNA was identified through an agarose gel electrophoresis, and concentrations and purities were measured by using a nanodrop device (Thermo scientific, Nanodrop Lite). The DNA thus obtained was used for expression.

Preparation Example 1-3. Expression of Fusion Proteins in CAP-T Cells

Human cell lines were transfected with each plasmid DNA type obtained in Preparation Example 1-2. Each plasmid DNA type was transduced into CAP-T cells (CEVEC), which had been cultured in PEM medium (Life technologies), by using PEI solution (Polyplus, Cat. No.: 101-10N). The mixed solution of DNA and the PEI solution was mixed with the cell suspension by using a FREESTYLE293™ expression medium (Invitrogen), cultured at 37° C. for 5 hours, and PEM medium was added. After culturing at 37° C. for 5-7 days, the culture was centrifuged to remove cells and a supernatant including FGF21 mutant fusion proteins was obtained.

Preparation Example 1-4. Expression and Purification of FGF21 Mutant Fusion Proteins in *E. coli*

*E. coli* strain BL21 (DE3) was transformed with each plasmid DNA expressing DFD6 (*E. coli*) and RGE (Amgen) fusion proteins. The transformed *E. coli* expressing each fusion protein was inoculated into 20 mL of LB media, cultured at 37° C. for 15 hours with shaking, and then a portion of the culture media was inoculated into 100 mL of LB media, and cultured at 37° C. for 16 hours with shaking. Upon completion of culturing, the culture was centrifuged to obtain *E. coli* pellets, and then cells were disrupted using a high pressure cell disruptor to obtain inclusion bodies.

The obtained inclusion bodies were purified by washing and elution, followed by a protein refolding process. Specifically, the obtained inclusion bodies were washed 2-3 times with a buffer solution (pH 8.0) containing 0.5% Triton X-100, 50 mM Tris, 1 mM EDTA and 0.1 M NaCl to remove bacterial protein, and then resuspended in 8 M urea buffer containing 8 M urea, 50 mM Tris and 1 mM DTT. Since the proteins in 8 M urea buffer were completely denatured, a protein refolding process was performed as follows.

To begin, 8 M urea buffer was gradually diluted with 20 mM glycine buffer solution (pH 9.0) to remove urea, and from the concentration of 2 M, $CuSO_4$ was added to the concentration of 80 μM to induce stable protein folding. The protein completing the refolding process was suspended in PBS buffer solution (pH 7.4), and the suspension was filtered with a 0.22 μm filter to remove impurities, and then loaded into a Protein A affinity chromatography column. The column was washed with 1×PBS buffer solution (pH 7.4) and then the proteins were eluted using 100 mM glycine buffer solution (pH 3.0) to prepare DFD6 (*E. coli*) fusion protein.

In the case of RGE (Amgen) fusion protein, the protein completing the refolding process was suspended in 50 mM Tris buffer solution (pH 8.0), the suspension was filtered with a 0.22 μm filter to remove impurities, and then loaded into an anion exchange resin column (POROS® HQ 50 μm, Thermo Fisher Scientific). The column was washed with 50 mM Tris buffer solution (pH 8.0), and then 50 mM Tris buffer solution (pH 8.0) was administered along the concentration gradient to elute RGE (Amgen) fusion protein. The RGE (Amgen) fusion protein obtained by the anion exchange resin was mixed with ammonium sulfate to the concentration of 1 M, and then purified using a hydrophobic interaction chromatography column (Phenyl sepharose FF, GE Healthcare). Specifically, the column was washed with 50 mM Tris buffer solution (pH 8.0) containing 1 M ammonium sulfate, 50 mM Tris buffer solution (pH 8.0) was administered along the concentration gradient, and the eluted fractions were analyzed through 10% Tris-glycine gel electrophoresis. The gel was dyed with coomassie brilliant blue R with mild shaking, and the fractions containing FGF21 mutant fusion protein with high purity were collected and then dialyzed overnight at 4° C. using a final buffer solution (1×PBS, 1 mM EDTA, pH 7.4). Upon completion of the dialysis, the obtained protein stock solution was concentrated at 3,000 rpm by using a 30,000 MW cut-off centrifugation filter at 4° C. The concentration of FGF21 mutant fusion protein was measured via BCA quantitative analysis.

Preparation Example 1-5. Purification of FGF21 Mutant Fusion Proteins

Protein A affinity chromatography column (GE Healthcare) was equilibrated with 1×PBS buffer solution (pH 7.4). The culture supernatant including each FGF21 mutant fusion protein obtained in Preparation Example 1-3 was filtered with a 0.2 μm filter, and then loaded into a Protein A affinity chromatography column. The column was washed with 1×PBS buffer solution (pH 7.4) and then proteins were eluted using 100 mM glycine buffer solution (pH 3.0). The fusion proteins obtained by affinity chromatography were purified using an anion exchange resin column (POROS® HQ 50 μm, Thermo Fisher Scientific). The anion exchange resin column was equilibrated with 50 mM Tris buffer solution (pH 8.0), before the FGF21 mutant fusion proteins were eluted from the column. Specifically, after washing the column with 50 mM Tris buffer solution (pH 8.0), 50 mM Tris buffer solution (pH 8.0) was dispensed along the concentration gradient and the eluted fractions were analyzed. Each eluted fraction was analyzed using size exclusion chromatography (SEC-HPLC), and the fractions including FGF21 mutant fusion proteins with high purity were collected. The concentration and quantitative analysis were performed in accordance with the methods described in Preparation Example 1-4.

Experimental Example 1. In Vitro Activities of Fusion Proteins

Experimental Example 1-1. Effect of FGF21 Mutations on Protein Activity

The in vitro activities of fusion proteins DFD4, DFD5, DFD6, DFD6 (*E. coli*), DFD7, DFD9, DFD13, DFD18, DFD72, DFD73 and DFD74 prepared in Preparation Example 1 were measured.

Specifically, the in vitro FGF21 activities of the fusion proteins were evaluated using a HEK293 cell line (Yuhan Corporation, Korea) which was modified to overexpress human β-klotho, a coreceptor of FGF21. For the evaluation of activity, the concentrates containing the fusion proteins prepared in Preparation Examples 1~4 and 1-5 were subjected to a 3-fold serial dilution at a concentration of 3 μM. After having been cultured in a serum-deficient state for 5 hours, the cell line overexpressing human β-klotho was treated with the diluted fusion proteins for 20 minutes, and then were lysed by adding cytolysis buffer (Cisbio/Cat #64ERKPEG) with stirring at 60 rpm for 30 minutes at room temperature. The cell lysate solution was mixed with antibodies (Cisbio/Cat #64ERKPEG), which can detect extracellular signal-regulated kinase (ERK) and phosphorylated ERK, and the mixture was maintained at room temperature for 2 hours. Fluorescence was detected using a fluorometric detector (TECAN/GENiosPro). The activities of the fusion proteins were measured by comparing their $EC_{50}$ values.

Figure 1B:
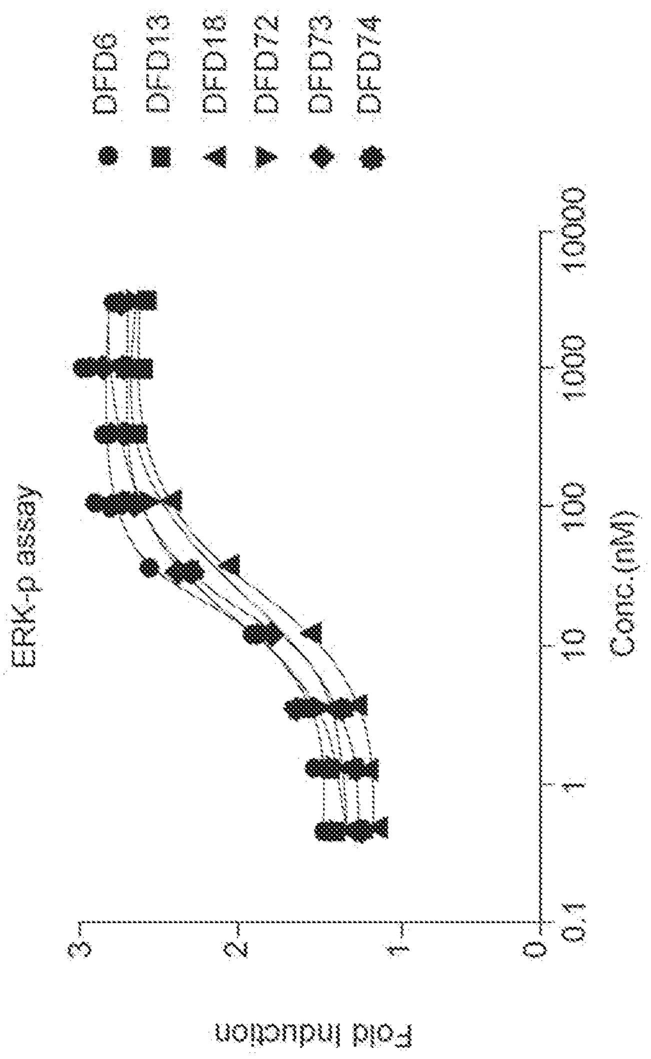
Figure 1C:
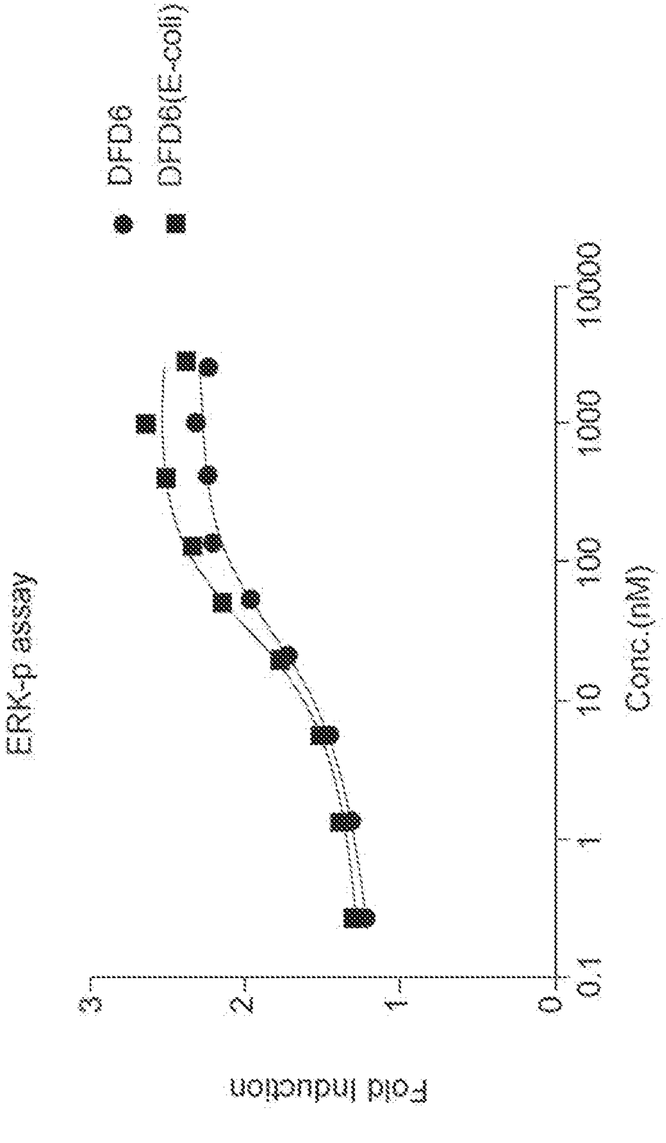

As shown in FIGS. 1A to 1C, it was confirmed that the in vitro activities of the fusion proteins prepared by introducing mutation sequences into the wild-type FGF21 protein were not inhibited, and the activities of each fusion protein were similar to each other. It was also confirmed that through the DFD6 (*E. coli*) sample expressed in *E. coli* and the DFD6 sample expressed in animal cells, the in vitro activities of the fusion proteins prepared by introducing N-glycosylation mutation into the wild-type FGF21 protein were not inhibited.

Experimental Example 1-2. Effect of Linker Sequence on Protein Activity

The in vitro activities of fusion proteins DFD1, DFD3, DFD4 and DFD13 prepared in Preparation Example 1 were measured.

Specifically, the FGF21 activities of the fusion proteins were measured by using the concentrates containing the fusion proteins prepared in Preparation Example 1-5 in accordance with the methods described in Experimental Example 1-1. The results are shown in FIGS. 2A and 2B.

Figure 2A:
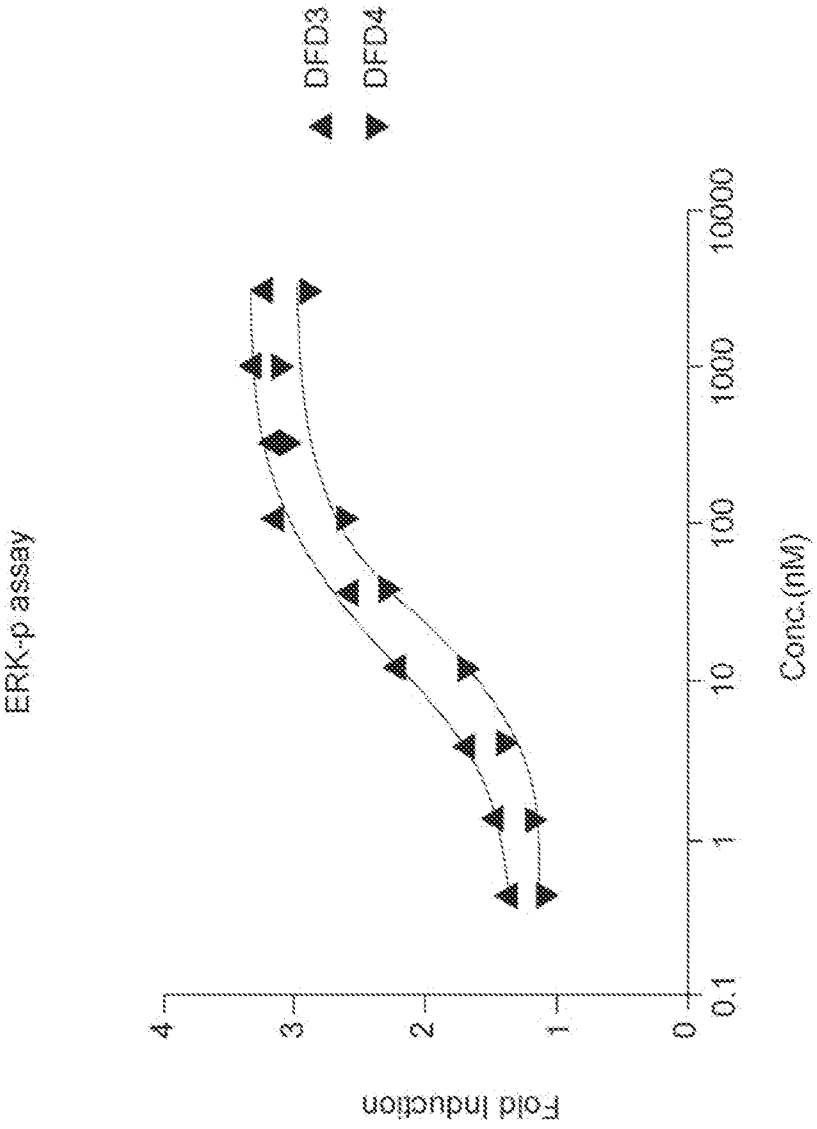
FIGS. 2A and 2B are graphs showing the measurement results of in vitro activities of FGF21 mutant fusion proteins depending on linkers which connect the N-terminus of FGF21 to an Fc region by using the HEK293 cell line in which human β-klotho is overexpressed. No FGF21 mutant fusion protein variants showed a significant decrease in activity, although slight differences were observed in terms of activity depending on the linker sequence.
Figure 2B:
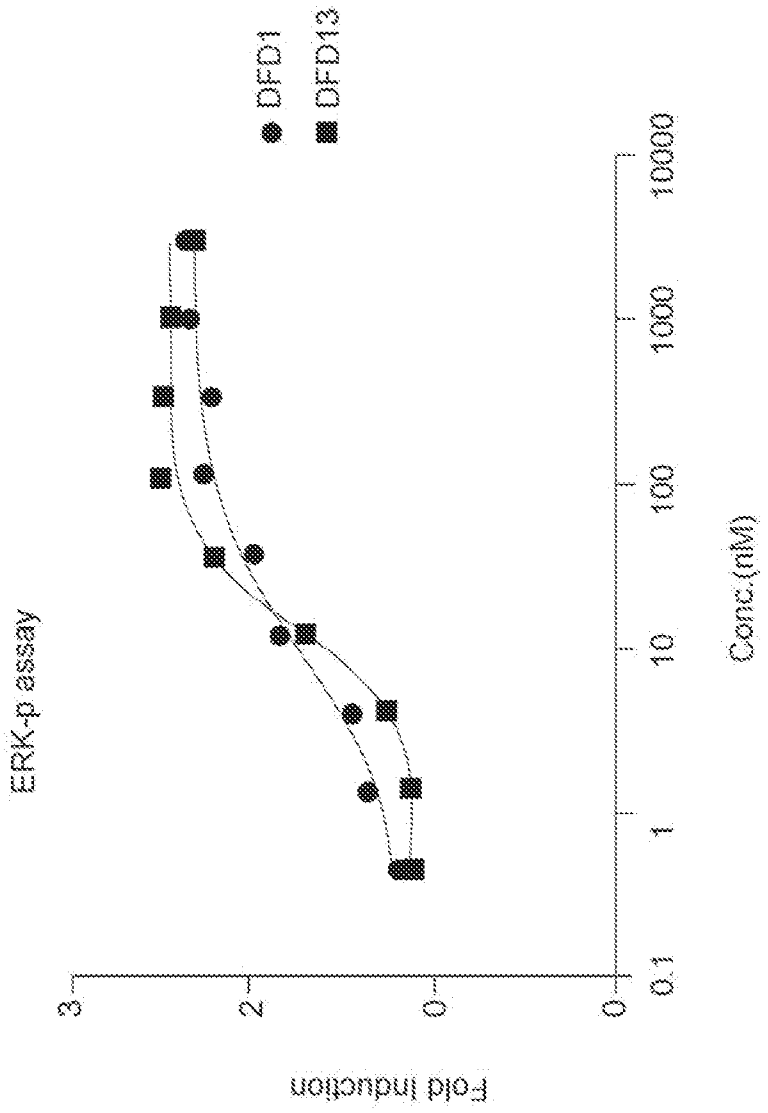

It was confirmed that no FGF21 mutant fusion protein showed a significant decrease in the activity, although a slight difference was shown in the activity depending on the linker sequence, as shown in FIGS. 2A and 2B.

Experimental Example 1-3. Experimental Results for DFD1, RGE (Amgen) and Fc-FGF21 (Lilly)

The in vitro activities of fusion protein DFD1 prepared in Preparation Example 1 and control proteins RGE (Amgen) and Fc-FGF21 (Lilly) were measured.

Specifically, the FGF21 activities of the fusion proteins were measured by using the concentrates containing the fusion proteins prepared in Preparation Example 1-5 and the control proteins in accordance with the methods described in Experimental Example 1-1. The results are shown in FIG. 3.

Figure 3:
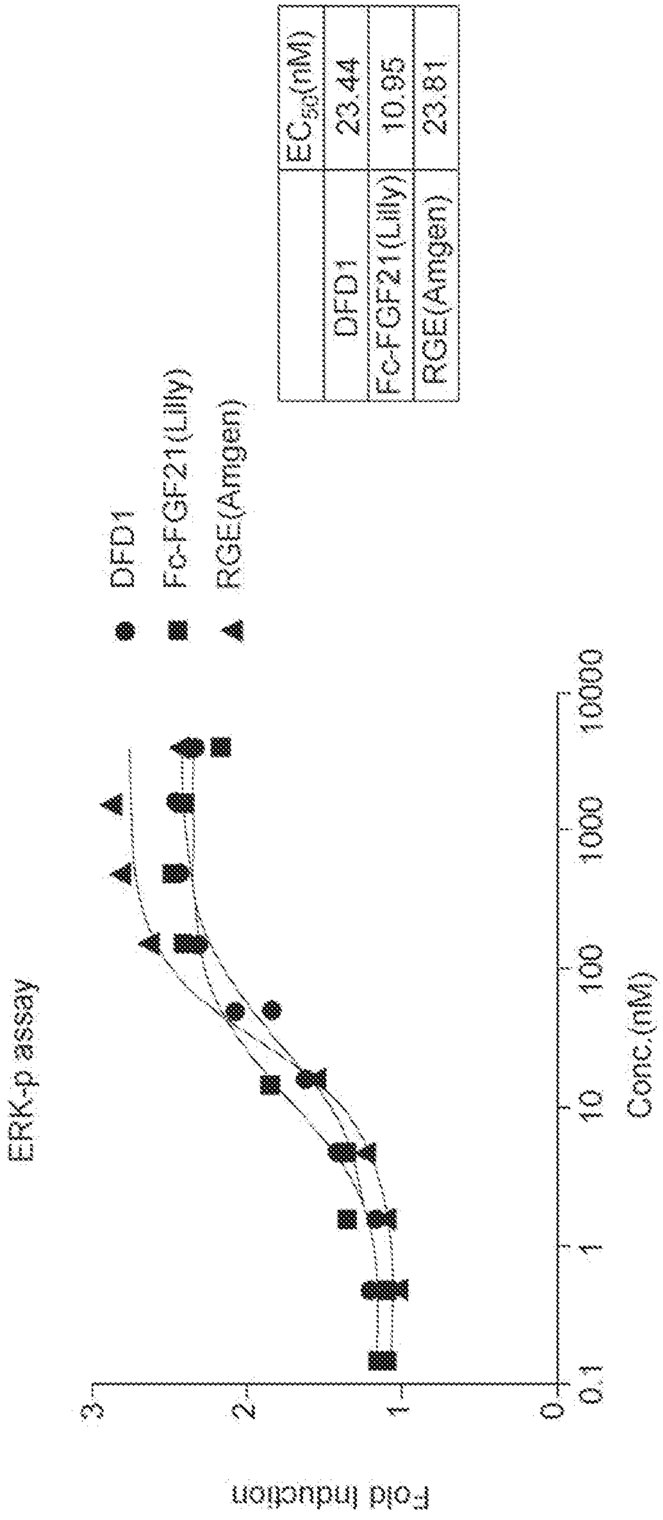
FIG. 3 is a graph showing the measurement results of in vitro activities of RGE (Amgen), Fc-FGF21 (Lilly) and DFD1 using the HEK293 cell line in which human β-klotho is overexpressed. DFD1 and RGE (Amgen) had similar activities, while Fc-FGF21 (Lilly) had in vitro activity two times higher than the other proteins.

It was confirmed that DFD1 and RGE (Amgen) had similar in vitro activity, while Fc-FGF21 (Lilly) had in vitro activity two times higher than those of the other proteins, as shown in FIG. 3.

Experimental Example 2. Evaluation of Stability of Fusion Proteins

Experimental Example 2-1. Experimental Method for Evaluating Stability

In order to measure the quantity of protein aggregates at the initial stage of the sample preparation, high molecular weight aggregates (% HMW) were quantified using a size-exclusion chromatography (SEC-HPLC) method. The results are shown in FIGS. 4A-4C.

Specifically, a TosoHaas model TSK-GEL™ G3000SW$_{XL}$ column was used for the SEC-HPLC method. The column was equilibrated by flowing a buffer solution (1×PBS, 1 mM EDTA, pH 7.4) at a flow rate of 1 mL/min. The DFD4 and DFD13 protein stock solutions prepared in Preparation Examples 1-5 were concentrated to a target concentration of 20 mg/mL or higher at 3,000 rpm using a 30,000 MW cut-off centrifugation filter at 4° C. After the measurement of the concentration of each sample by BCA quantitative analysis, the samples were diluted with a buffer solution (1×PBS, 1 mM EDTA, pH 7.4) to a final concentration of 20 mg/mL. In order to measure the initial % HMW of DFD4 and DFD13, 20 mg/mL of the samples were diluted with the buffer solution (1×PBS, 1 mM EDTA, pH 7.4) to a final concentration of 1 mg/mL, and each sample in a volume of 100 μL was analyzed by SEC-HPLC column.

For the stability evaluation of each sample, % HMW of the samples was measured using the SEC-HPLC method on the 4$^{th}$, the 8$^{th}$ and the 14$^{th}$ days while storing them at 5° C., 25° C. and 37° C. for two weeks.

Figure 4A:
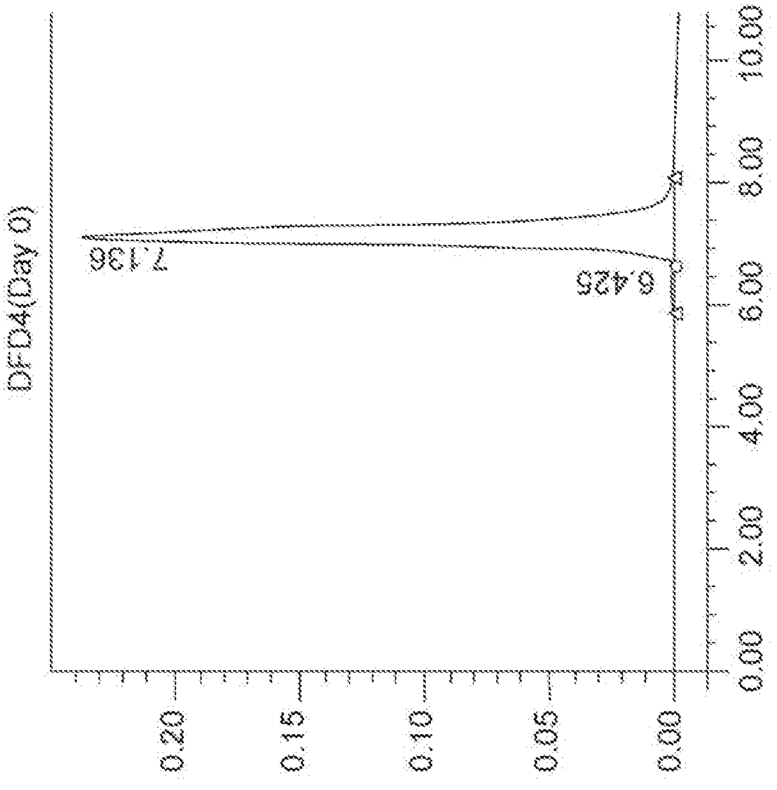
FIG. 4A, FIG. 4B, and FIG. 4C are graphs comparing the stability of DFD4 with that of DFD13 in order to confirm the effect of the EIRP (SEQ ID NO: 42) mutation (in FGF21) on the stability of fusion protein. It was confirmed that DFD13 had a lower rate of high molecular weight aggregates (HMW %) at the initial stage and at a time-point of more than 2 weeks as compared with DFD4, which indicates that the introduction of the EIRP (SEQ ID NO: 42) mutation improves the stability of the FGF21 mutant fusion protein, thereby reducing HMW % significantly.
Figure 4B:
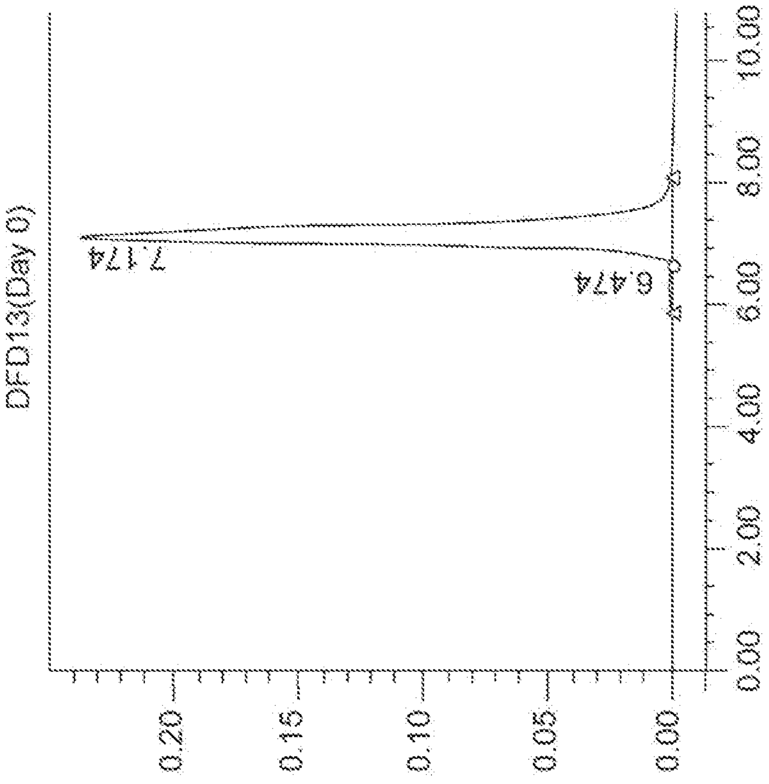
Figure 4C:
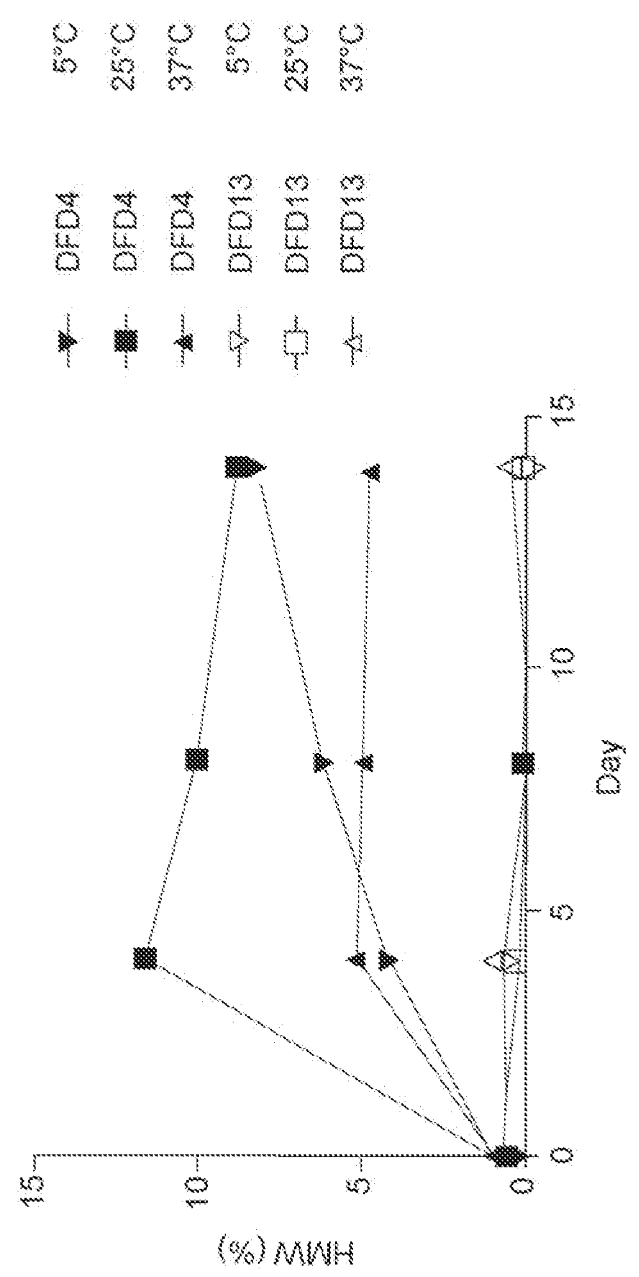

As shown in FIGS. 4A-4C, it was confirmed that DFD13 had a lower quantity of high molecular weight aggregates (HMW %) at the initial stage and up to the point of 2 weeks as compared with DFD4, indicating that the introduction of the EIRP (SEQ ID NO: 42) mutation improves the stability of the FGF21 mutant fusion protein, thereby reducing HMW % significantly.

Experimental Example 2-2. Stability Results

In order to investigate the effects of the EIRP mutation introduced into the original sequence LLLE (98-101) (SEQ ID NO: 58) of FGF21 on stability, the stability of DFD4 (SEQ ID NO: 29) and DFD13 (SEQ ID NO: 35) was measured in accordance with the methods described in Experimental Example 2-1. The analysis results for the zero-hour sample (initial stage; Day 0) and 4-, 8-, and 14 day-stored samples of DFD4 and DFD13 are summarized in Table 4 below (in Table 4, N.D. means "not detected").

TABLE 4

Stability of DFD4 and DFD13 for 2 weeks at a concentration of 20 mg/mL (% HMW)

| | DFD4 | | | DFD13 | | |
|---|---|---|---|---|---|---|
| Day | 5° C. | 25° C. | 37° C. | 5° C. | 25° C. | 37° C. |
| 0 | | 0.91 | | | 0.56 | |
| 4 | 4.25 | 11.64 | 5.12 | 0.36 | 0.34 | 0.84 |
| 8 | 6.16 | 9.99 | 4.87 | N.D. | N.D. | N.D. |
| 14 | 8.15 | 8.83 | 4.71 | N.D. | N.D. | 0.32 |

As shown in Table 4, the quantity of % HMW at the initial stage (Day 0) was 0.91% for DFD4, and 0.56% for DFD13. After 2 weeks, the amount of % HMW increased to 8.83% for DFD4, but it was not observed in DFD13, under the condition of storage at 25° C. DFD13 was shown to have a lower % HMW rate at the initial stage and 2 weeks, as compared with DFD4, which indicates that the % HMW rate of FGF21 mutant fusion protein decreased significantly due to the introduction of the EIRP mutation.

Experimental Example 3. Pharmacokinetic Assessment of Fusion Proteins

Experimental Example 3-1. Experimental Method for Pharmacokinetic Assessment

Six-week old male ICR mice purchased from Orient BIO (Korea) were partitioned into groups (n=3/blood sampling time) in order to have similar mean values for body weight one day before drug treatment, and subcutaneously administered once with a respective sample at 1 mg/kg (2 mg/kg for RGE). Blood samples were then collected at 1, 4, 8, 12, 24, 48, 72, and 96 hours after the injection, respectively. The concentration of intact full length FGF21 protein in the blood was measured using a Intact human FGF21 ELISA Kit (F1231-K01, Eagle Biosciences, USA), which has immunoreactivity to the N-terminus and C-terminus of FGF21 protein. The concentrations of the samples in the blood collected until 96 hours after the subcutaneous injection of each fusion protein into the mice were measured, and pharmacokinetic parameters of each sample were calculated.

Experimental Example 3-2. Assessment of Pharmacokinetic Activity

Figure 5:
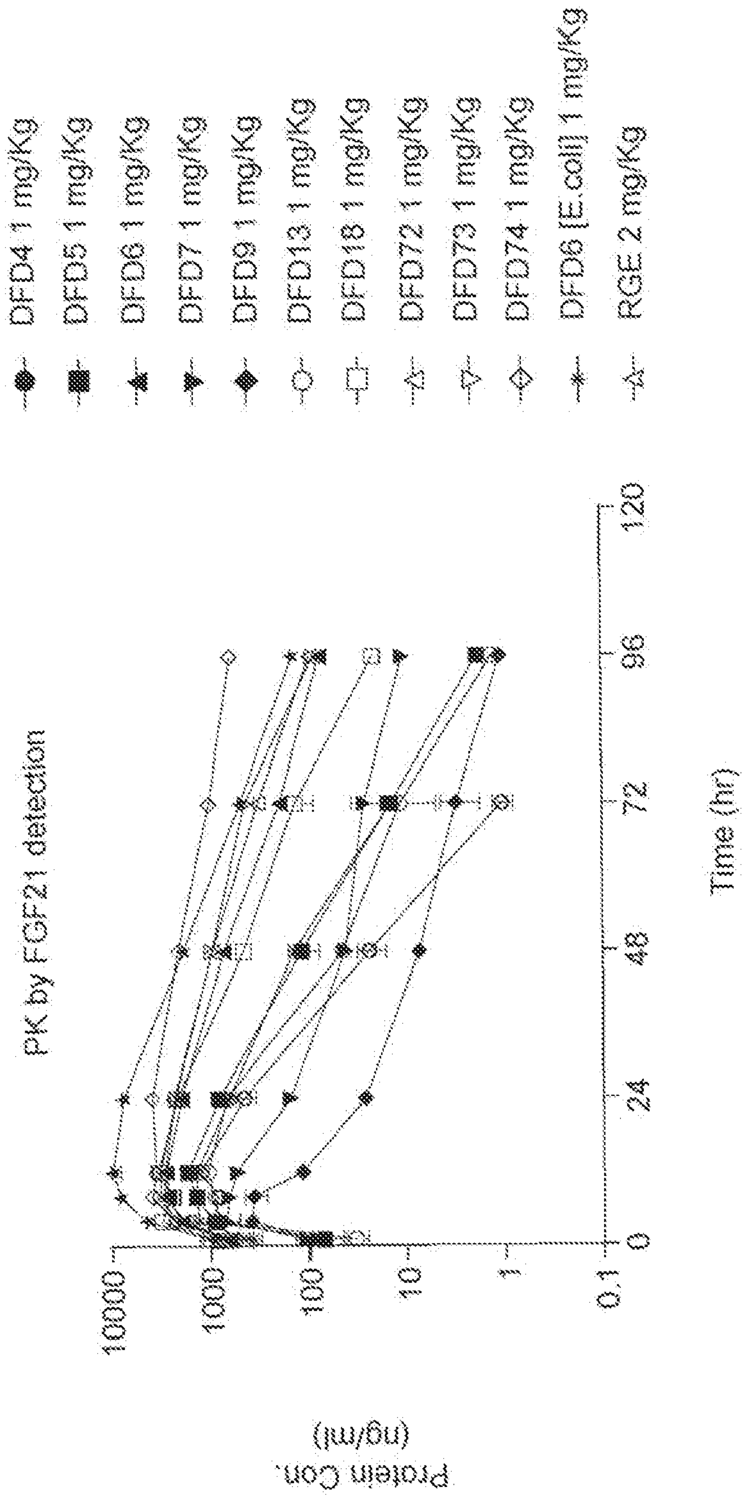
FIG. 5 is a graph showing the concentration of each protein in the blood over 96 hours after subcutaneous administration of FGF21 mutant fusion proteins. Data are indicated as mean values and standard deviation.

Based on the graph showing the concentrations of each protein in the blood versus time after the subcutaneous administration of fusion proteins in mice (FIG. 5), the pharmacokinetic parameters were calculated. The data are shown in Table 5 below.

TABLE 5

| Parameters | DFD4 | DFD5 | DFD6 | DFD7 | DFD9 | DFD13 | DFD18 | DFD72 | DFD73 | DFD74 | DFD6 (*E.coli*) | RGE* |
|---|---|---|---|---|---|---|---|---|---|---|---|---|
| $T_{max}$ (hour) | 12 | 12 | 12 | 4 | 4 | 12 | 12 | 8 | 8 | 8 | 8 | 12 |
| $C_{max}$ (ng/mL) | 1288 | 1732 | 2868 | 696 | 384 | 1070 | 3428 | 2962 | 3296 | 3996 | 1399 | 9921 |
| $AUC_{last}$ (ng · hr/mL) | 25856 | 40706 | 100107 | 14118 | 4656 | 28785 | 104230 | 115977 | 123511 | 206634 | 37269 | 325747 |
| Half-life (hour) | 5.5 | 8.0 | 14.9 | 19.7 | 17.4 | 7.1 | 11.0 | 14.4 | 16.6 | 26.0 | 9.1 | 12.9 |

The pharmacokinetic profile of each fusion protein was compared and evaluated based on the value of the area under the curve (AUC) indicating the degree of drug exposure.

As shown in Table 5, upon comparing DFD4 with DFD13, and DFD6 with DFD73, it was determined that the introduction of the EIRP sequence (SEQ ID NO: 42) resulted in an approximate 10 to 20% increase in AUC value. Comparing DFD9 with DFD4, the introduction of TGLEAV (SEQ ID NO: 43) resulted in an approximate 6-fold increase in AUC value.

Furthermore, the mutations of TGLEAN (SEQ ID NO: 44), G170N and G174N are designed to extend the half-life by introducing N-glycosylation into the C-terminus of FGF21, which is known to be proteolyzed in vivo. The increase in AUC due to the introduction of N-glycosylation was confirmed by comparing the mutants with each control material. In order to confirm the effect of improvement in AUC due to the introduction of N-glycosylation, the AUC value for DFD6 (*E. coli*) produced by *E. coli* which has no glycosylation was compared with that in DFD6 produced by a human cell line. DFD6 produced by the human cell line showed a 3-fold or higher increase in the AUC value as compared with DFD6 (*E. coli*) produced by *E. coli*, which demonstrated an improvement of pharmacokinetic profile due to glycosylation.

The A180E is a mutation disclosed in WO 2009/149171 owned by Amgen Inc. When the mutation of A180E was further introduced into the mutant DFD13 or DFD73 including the mutation of TGLEAV (SEQ ID NO: 43) or G170N, respectively, the resulting mutant DFD18 or DFD74, respectively, showed an approximate 2- to 3-fold additional increase in AUC value.

In summary, it was confirmed that the pharmacokinetic parameters were improved by the introduction of various mutations and combinations thereof, as compared with DFD9, the wild-type FGF21 fusion protein. The fusion protein showing the most improved AUC value was DFD74 containing the mutations of EIRP (SEQ ID NO: 42), G170N and A180E, which showed an approximate 45-fold improvement in AUC value as compared with DFD9. Furthermore, considering RGE (Amgen) at the dose of 2 mg/kg of body weight, DFD74 may have a higher degree of drug exposure as compared with RGE. The overall effects of improvement in pharmacokinetics due to the mutations are summarized in Table 6 below.

TABLE 6

| Mutation sequence | Position of mutation | Control material vs improved material | Assessment of pharmacokinetic parameters |
|---|---|---|---|
| EIRP (SEQ ID NO: 42) | 98-101 | DFD4 vs DFD13<br>DFD6 vs DFD73 | Improvement of AUC |
| TGLEAV (SEQ ID NO: 43) | 170-174 | DFD9 vs DFD4 | Improvement of AUC |
| TGLEA<u>N</u> (SEQ <u>ID</u> NO: 44) | 170-174 | DFD9 vs DFD5 | Improvement of AUC |
| G170<u>N</u> | 170 | DFD9 vs DFD6 | Improvement of AUC |
| | | DFD6 (*E. coli*) vs DFD6 | Improvement of AUC |
| G174<u>N</u> | 174 | DFD9 vs DFD7 | Improvement of AUC |
| A180E | 180 | DFD13 vs DFD18 | Improvement of AUC |
| | | DFD73 vs DFD74 | Improvement of AUC |

Experimental Example 4. Activity Evaluation of Fusion Proteins in Ob/Ob Mice

Experimental Example 4-1. Experimental Method for Evaluating Activity in Ob/Ob Mice The ob/ob mice, characterized as exhibiting hyperglycemia, insulin resistance, hyperphagia, fatty liver and obesity due to a genetic deficiency in leptin, are widely used for the study of type 2 diabetes. Male ob/ob mice (Harlan, USA) were purchased from Raonbio (Korea). These mice were 5 to 6 weeks old at the time of arrival, and 8 to 9 weeks old at the time of drug treatment after 3 weeks of adaptation. The mice were partitioned into groups (n=8/group) in order to have similar mean values for body weight and caudal blood glucose levels one day before the drug treatment (Day 0), and the samples were subcutaneously administered once according to each of their respective dosages. Dulbecco's phosphate buffered saline (DPBS, Gibco, USA) was administered as the vehicle treatment, and the glucose concentration in the blood was measured using a glucose meter, GLUCODRIM (All Medicus, Korea). The non-fasting glucose levels and body weights were measured every day until the 14$^{th}$ day after administration. Glycated hemoglobin levels were also measured in each group before the administration and after the test. The glycated hemoglobin levels were calculated using a DCA™ 2000 HbA1c kit (Siemens, 5035C).

Experimental Example 4-2. Evaluation of Activity in Ob/Ob Mice

The changes in non-fasting blood glucose levels and body weights in male ob/ob mice were observed after single subcutaneous injection of 30 or 100 nmol/kg of DFD18 and DFD72, or 10, 30 or 100 nmol/kg of DFD74.

Figure 6:
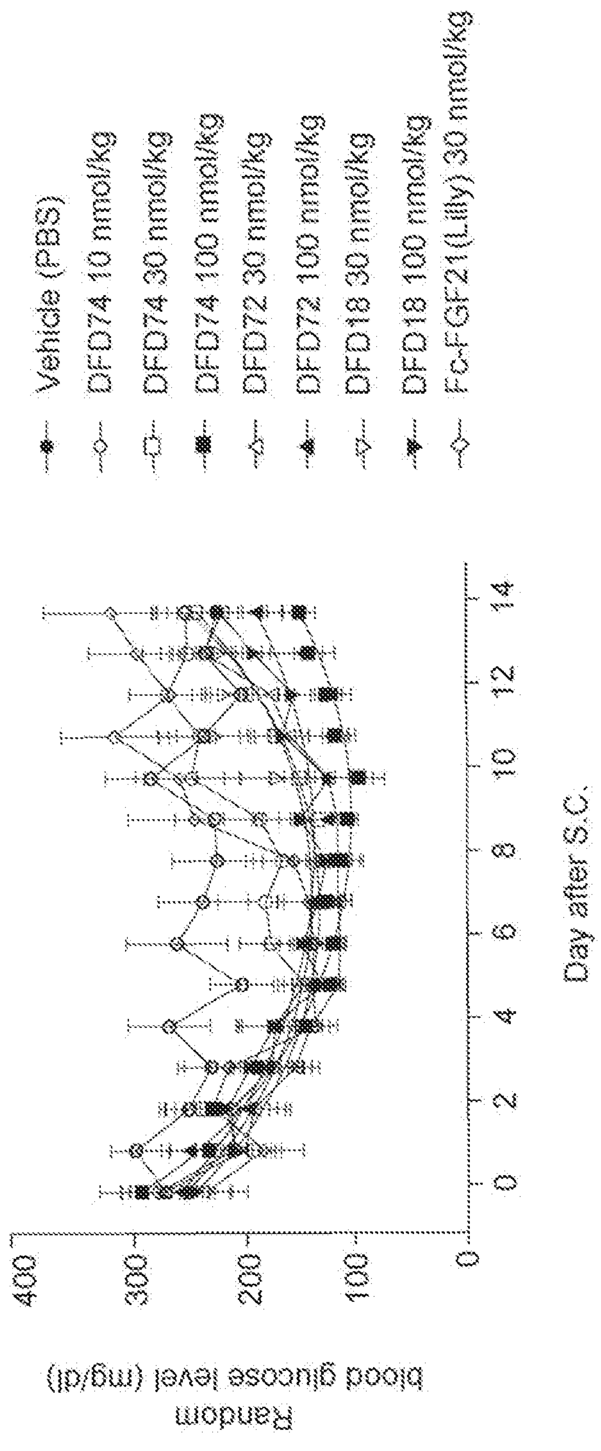
FIG. 6 is a graph showing the blood glucose levels in an ob/ob mouse model after single subcutaneous injection of DFD18, DFD72, DFD74 or Fc-FGF21 (Lilly). DFD18, DFD72 and DFD74 all had the effect of lowering blood glucose levels continuously. Data are indicated as mean values and standard error of the mean (S.E.M.).

It was confirmed that DFD18, DFD72 and DFD74 all had the effect of lowering blood glucose level in a dose-dependent manner. Comparing the three agents at the high dose of 100 nmol/kg, DFD72 and DFD74 showed an improved effect on lowering blood glucose level than DFD18 (FIG. 6). In addition, Fc-FGF21 (Lilly) which was used as a control material in the test, was less effective in lowing blood glucose level as compared with DFD18, DFD72 and DFD74 at the same dose level (30 nmol/kg).

Figure 7A:
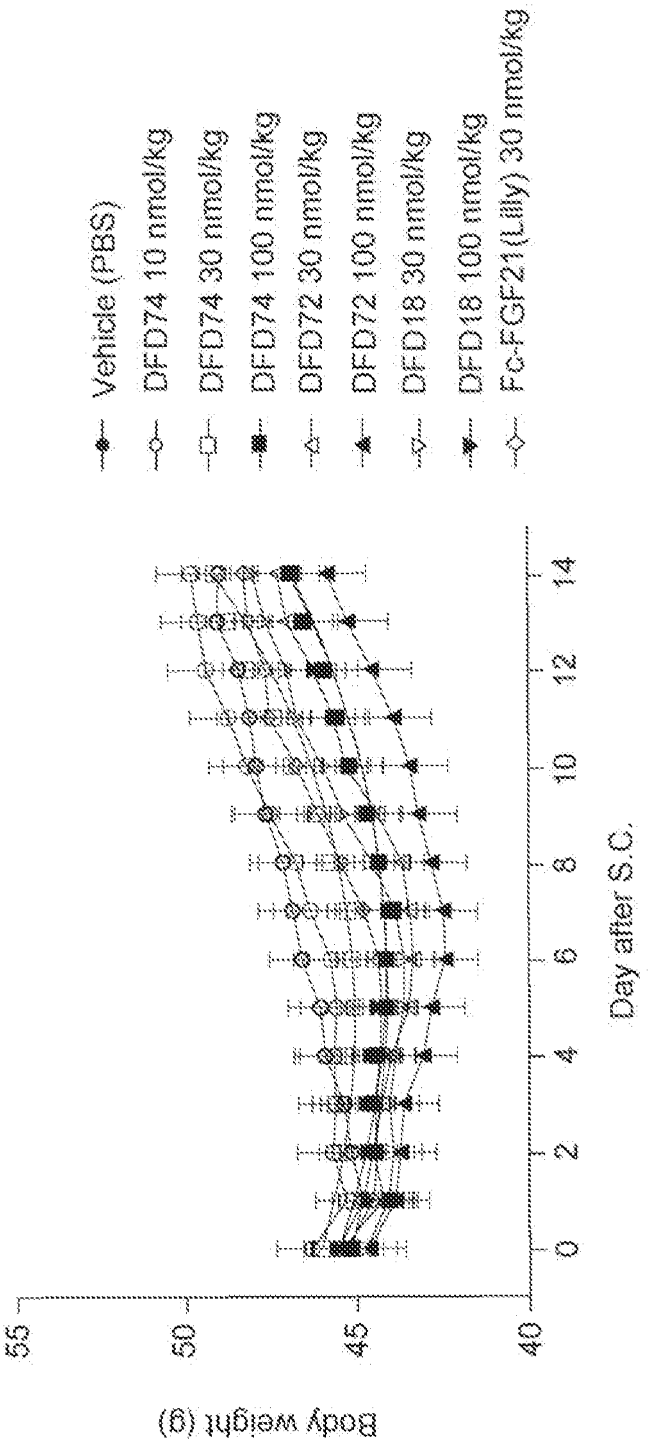
FIG. 7A and FIG. 7B are graphs indicating the changes in body weights in the ob/ob mouse model from the day of administration to the $14^{th}$ day after single subcutaneous injection of DFD18, DFD72, DFD74 or Fc-FGF21 (Lilly). DFD18, DFD72 and DFD74 all had the effect of reducing body weight as compared with the PBS-treated group. Data are indicated as mean values and standard error of the mean.
Figure 7B:
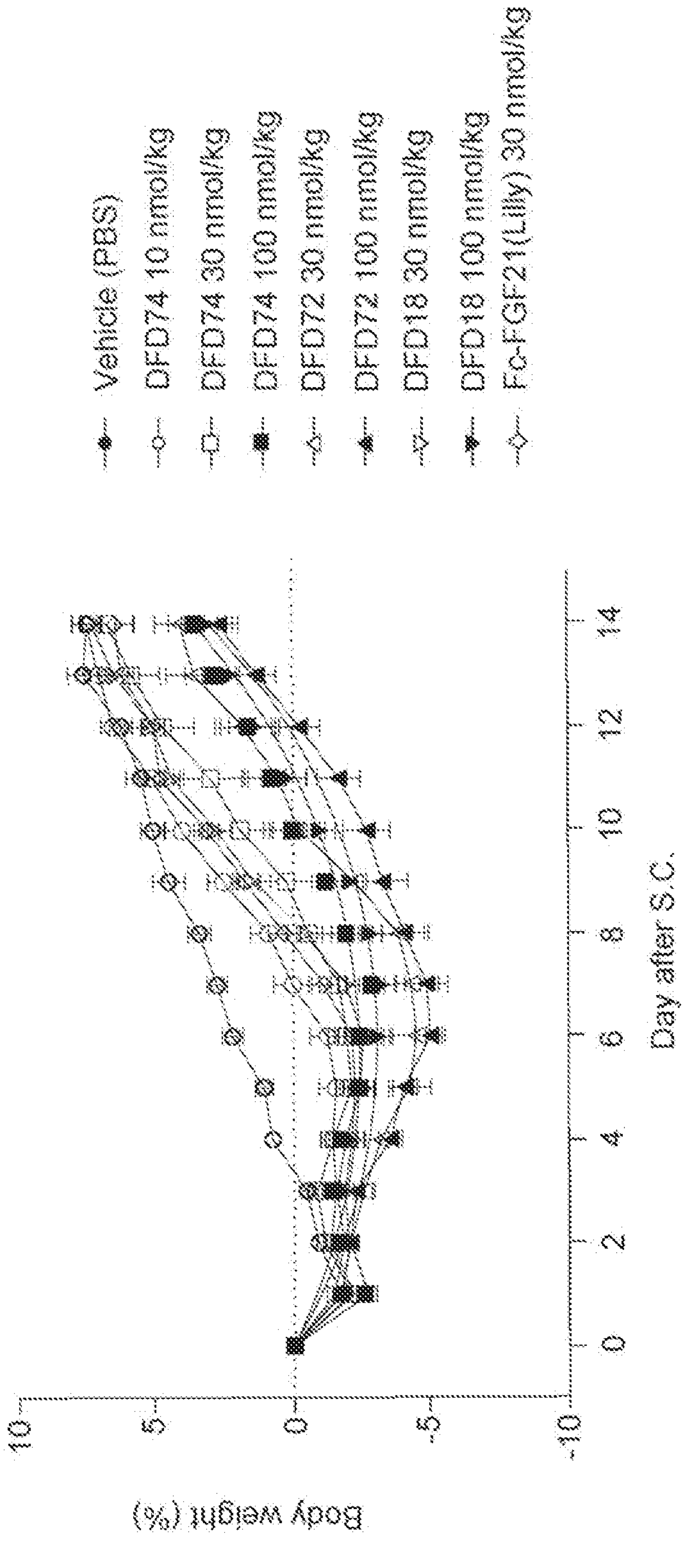

As for the effect on body weight reduction, comparing the three agents at the high dose of 100 nmol/kg, DFD72 was the most effective in ob/ob mice resulting in an approximate 6% reduction in body weight, and DFD18 was the next most effective, followed by DFD74 (FIGS. 7A and 7B).

Figure 8A:
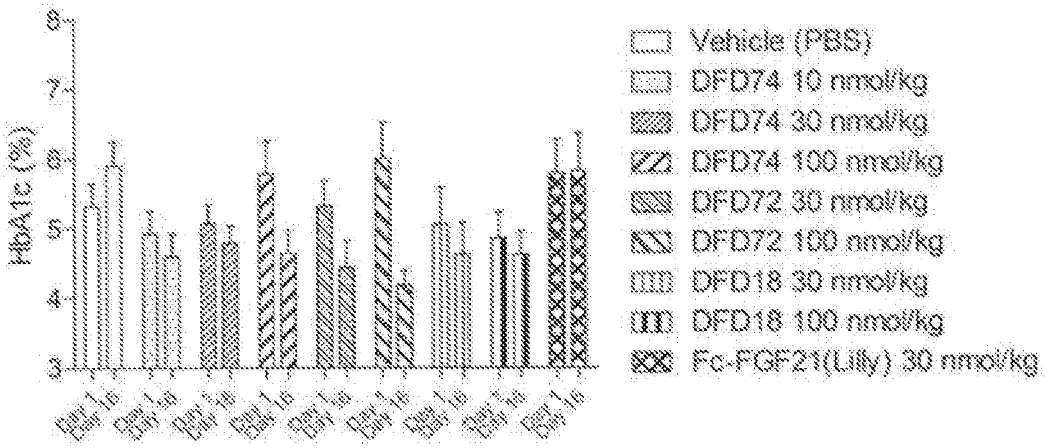
FIG. 8A and FIG. 8B are graphs indicating the changes in glycated hemoglobin levels in the ob/ob mouse model at the day of administration ($1^{st}$ day) and the $16^{th}$ day after single subcutaneous injection of DFD18, DFD72, DFD74 or Fc-FGF21 (Lilly). DFD18, DFD72 and DFD74 all caused reduced glycated hemoglobin levels at the 16th day as compared with those at the day of administration. Data are indicated as mean values and standard error of the mean.
Figure 8B:
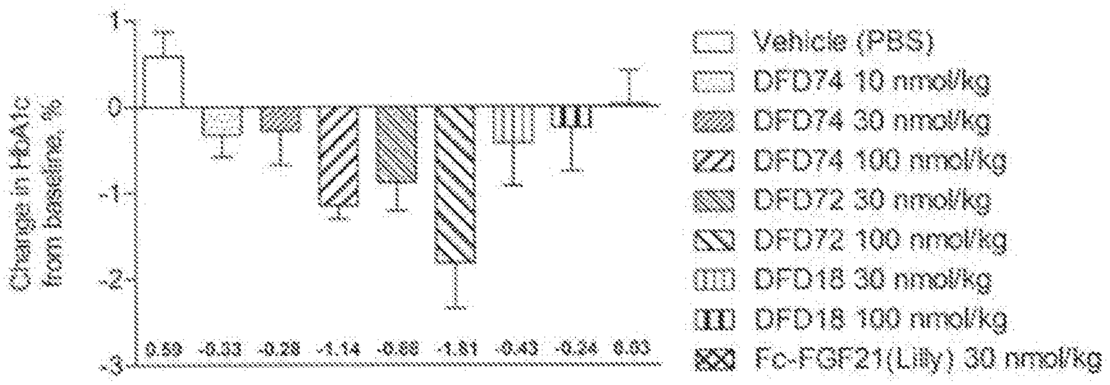

After the termination of the test, the glycated hemoglobin levels indicative of the mean values of blood glucose were measured and the changes in mean blood glucose were analyzed in each test group. All of the treated groups except the control group treated with control protein Fc-FGF21 (Lilly) showed negative values in the differences between before administration and after the test, which confirmed the effectiveness of the test proteins as compared with the control material in lowering blood glucose (FIGS. 8A and 8B).

Experimental Example 5. Activity Evaluation of Fusion Proteins in HFD/STZ Mice

Experimental Example 5-1. Experimental Method for Evaluating Activity in HFD/STZ Mice The effects of the FGF21 mutant fusion proteins on lowering blood glucose and body weight were compared and evaluated in another diabetic model, the HFD/STZ mouse model. Conventional dietary-induced obesity mouse models (induced by feeding 60 kcal % high fat diet to C57BL/6 mice for eight weeks or longer) have weak hyperglycemic and diabetic features, although they invoke insulin resistance. The HFD/STZ mice, which may compensate for defects in the conventional dietary-induced obesity mouse models, are capable of producing dysfunctional B cells in the pancreas and decreased secretion of insulin as a result of a high fat diet (HFD) and administration of low level streptozotocin (STZ), and are therefore useful for pharmacological studies of type 2 diabetes.

Specifically, in order to induce the HFD/STZ mouse model, C57BL/6 mice (Japan SLC) were fed on a 60 kcal % high fat diet for four weeks, and then 50 mg/kg of STZ (Sigma, 85882) was administered intraperitoneally every day for 3 days to induce dysfunction in the B cells of the pancreas. After feeding on the high fat diet for an additional 2 weeks, the mice with non-fasting blood glucose levels of 200 mg/dL or higher were used for the test. The mice were partitioned into groups (n=6/group) in order to have similar mean values of body weight and caudal blood glucose levels one day before the drug treatment (Day 0), and the samples were subcutaneously administered once according to each of their respective dosages. Dulbecco's phosphate buffered saline (DPBS, Gibco, USA) was administered as the vehicle treatment, and the glucose concentration in the blood was measured using a glucose meter, GLUCODRIM (All Medicus, Korea). The non-fasting glucose levels and body weights were measured every day until the 14$^{th}$ day after administration. Glycated hemoglobin levels were also measured in each group before the administration and after the test. The glycated hemoglobin levels were calculated using a DCA™ 2000 HbA1c kit (Siemens, 5035C).

Experimental Example 5-2. Activity Evaluation in HFD/STZ Mice

The changes in non-fasting blood glucose levels and body weights over time in male HFD/STZ mice were observed after single subcutaneous injection of 10 nmol/kg of DFD72 or DFD74.

Figure 9:
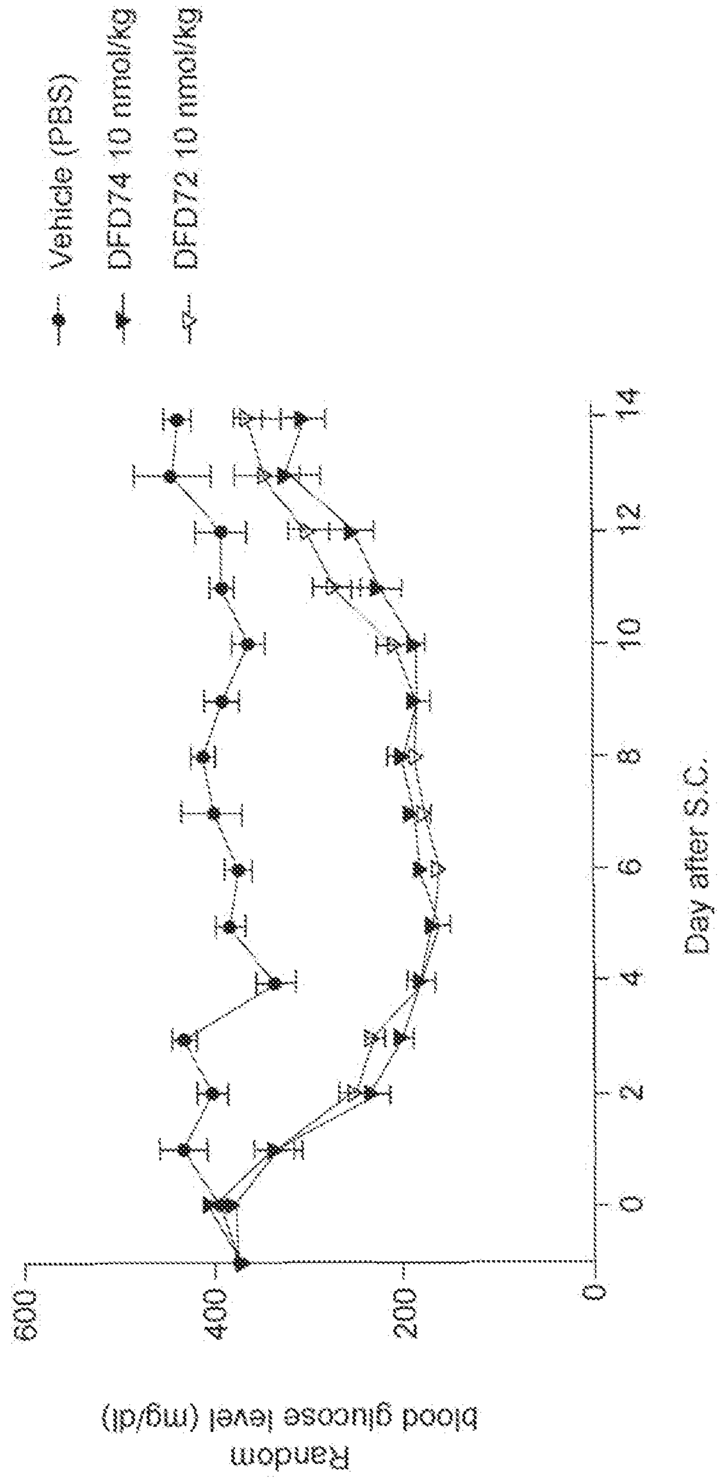
FIG. 9 is a graph showing the blood glucose levels in the HFD/STZ mouse model after single subcutaneous injection of DFD72 or DFD74. Both DFD72 and DFD74 had the effect of lowering blood glucose levels continuously. Data are indicated as mean values and standard error of the mean.

Regarding the changes in non-fasting blood glucose levels, it was confirmed that DFD72 and DFD74 had similar effects on lowering blood glucose levels, and the blood glucose lowering effect was maintained until the 10$^{th}$ day after administration and then lost with metabolism of the drugs after the 10$^{th}$ day (FIG. 9). DFD72 showed a more prolonged effect than DFD74 in terms of changes in non-fasting blood glucose levels after the 10$^{th}$ day after administration.

Figure 10A:
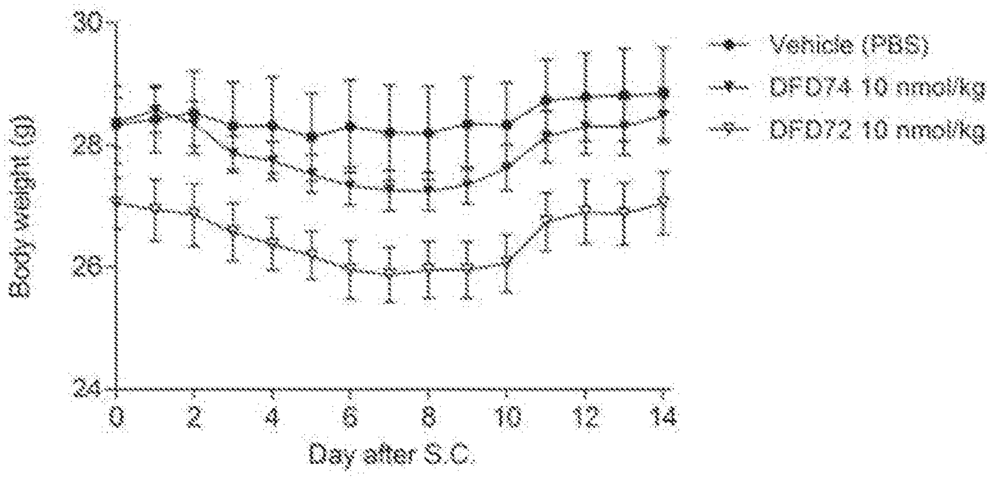
FIG. 10A and FIG. 10B are graphs indicating the changes in body weights in the HFD/STZ mouse model from the day of administration to the 14$^{th}$ day after single subcutaneous injection of DFD72 or DFD74. Both DFD72 and DFD74 had the effect of reducing body weight as compared with the PBS-treated group. Data are indicated as mean values and standard error of the mean.
Figure 10B:
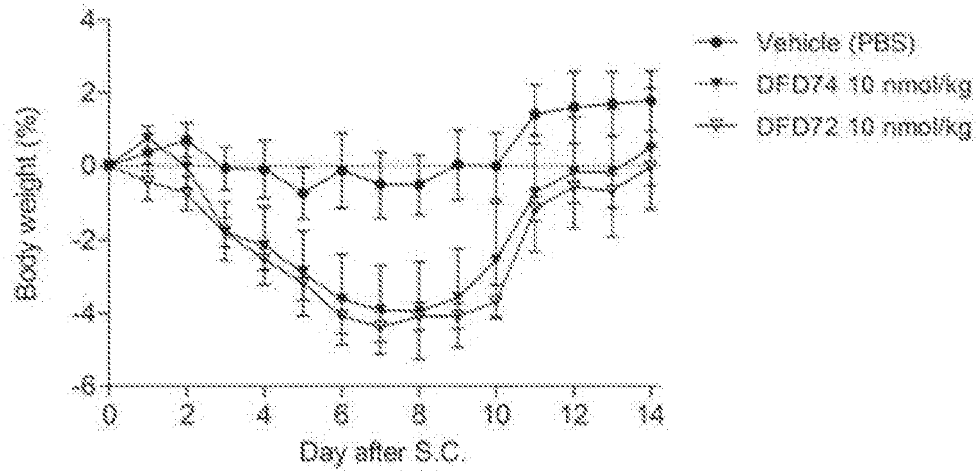

In terms of the effect on body weight reduction due to the administration of FGF21 mutant proteins, it was confirmed that both DFD72 and DFD74 had similar effects on reducing body weight by approximately 5%, and the effect disappeared after the 10$^{th}$ day after administration (FIGS. 10A and 10B).

Figure 11A:
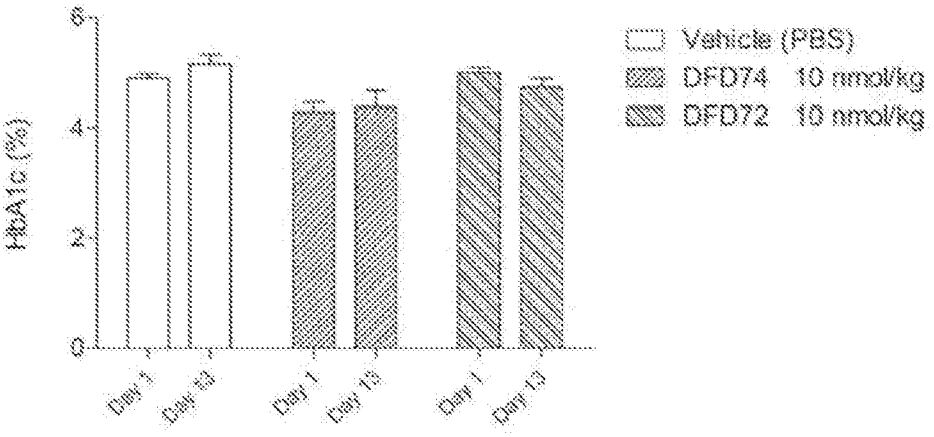
FIG. 11A and FIG. 11B are graphs indicating the changes in glycated hemoglobin levels in the HFD/STZ mouse model at the 1$^{st}$ day and the 13$^{th}$ day after single subcutaneous injection of DFD72 or DFD74. It was shown that both DFD72 and DFD74 treatment resulted in a greater reduction of glycated hemoglobin levels as compared with the PBS-treated group. Data are indicated as mean values and standard error of the mean.
Figure 11B:
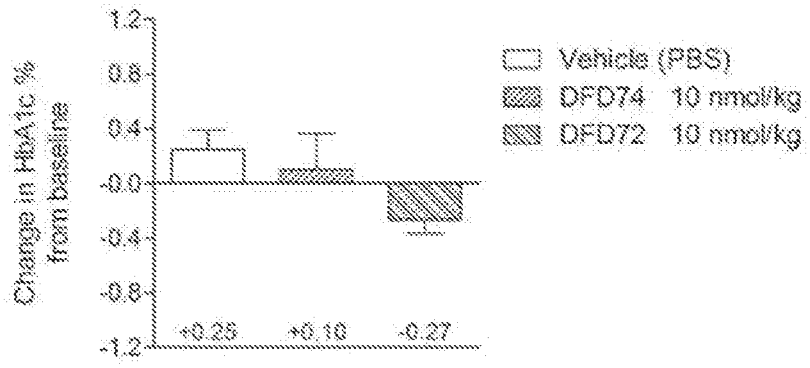

After the termination of the test, the glycated hemoglobin levels indicative of the mean value of blood glucose were measured and the changes in mean blood glucose were analyzed in each test group. While the vehicle group had an increase of 0.25 in glycated hemoglobin levels, the group treated with DFD74 had an increase of 0.1 and the group treated with DFD72 had an decrease of 0.27 (FIGS. 11A and 11B).

Experimental Example 6. Activity of Fusion Proteins in Diet-Induced Obese Mice

Experimental Example 6-1. Experimental Method for Evaluating Activities in Diet-Induced Obese Mice The body weight-reduction effect of DFD18, an FGF21 mutant fusion protein, was evaluated in diet-induced obese mice. For the diet-induced obesity model, C57BL/6J mice were purchased from Central Lab. Animal Inc. and fed on a high-fat diet containing 60 kcal % fat (Research diet) for 8 to 12 weeks. The mice were partitioned into groups (n=8/group) in order to have a similar mean value of body weight one day before the drug treatment (Day 0), and then 30 nmol/kg of samples were subcutaneously administered once. The changes in body weights were compared with the group treated with vehicle (PBS).

Experimental Example 6-2. Protein Activity in Diet-Induced Obese Mice

Figure 12A:
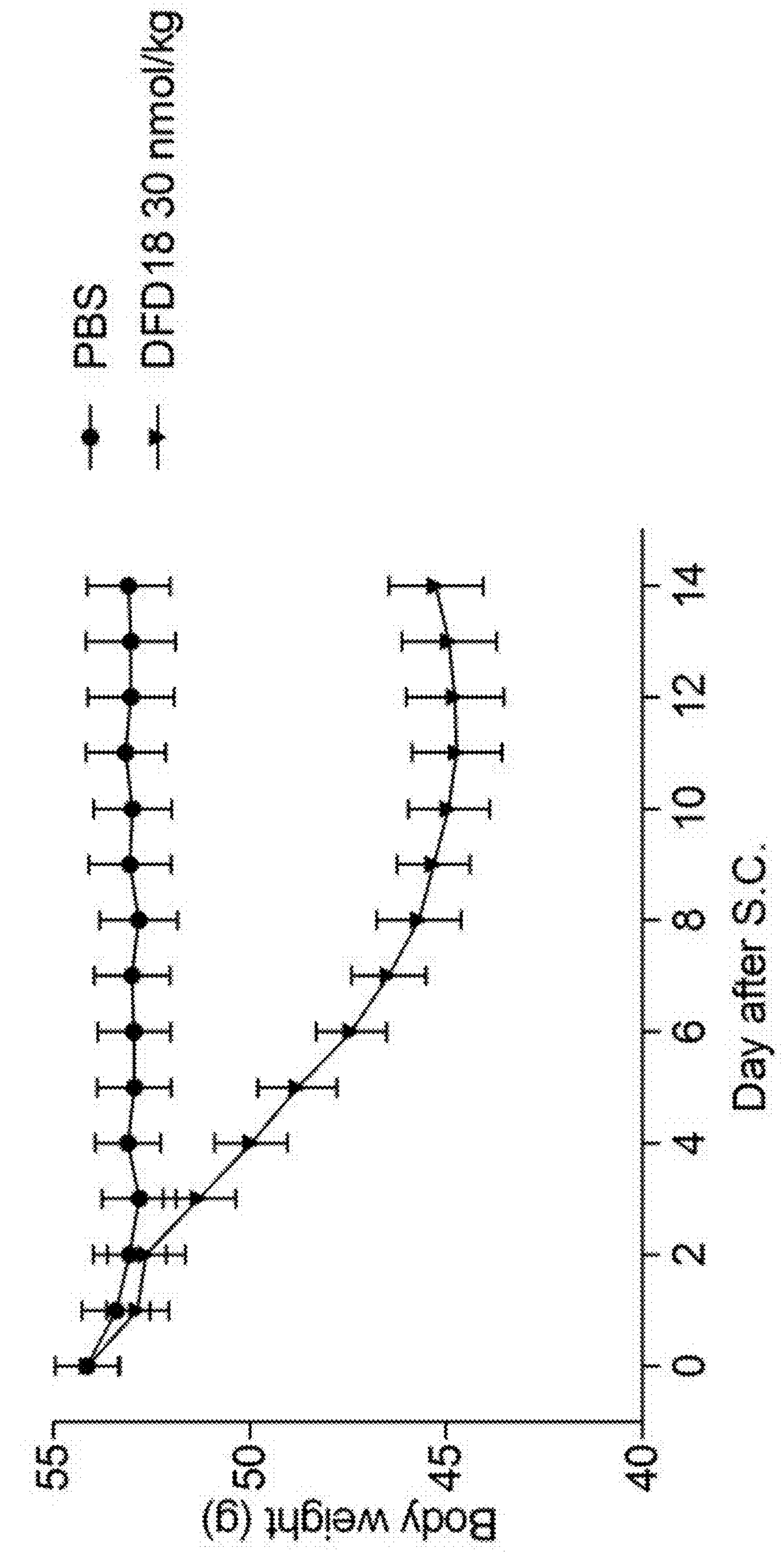
FIG. 12A and FIG. 12B are graphs indicating the changes in body weights measured in a diet-induced obesity mouse model from the day of administration to the 14$^{th}$ day after single administration of DFD18. DFD18 had an excellent effect on body weight reduction. Data are indicated as mean values and standard error of the mean.
Figure 12B:
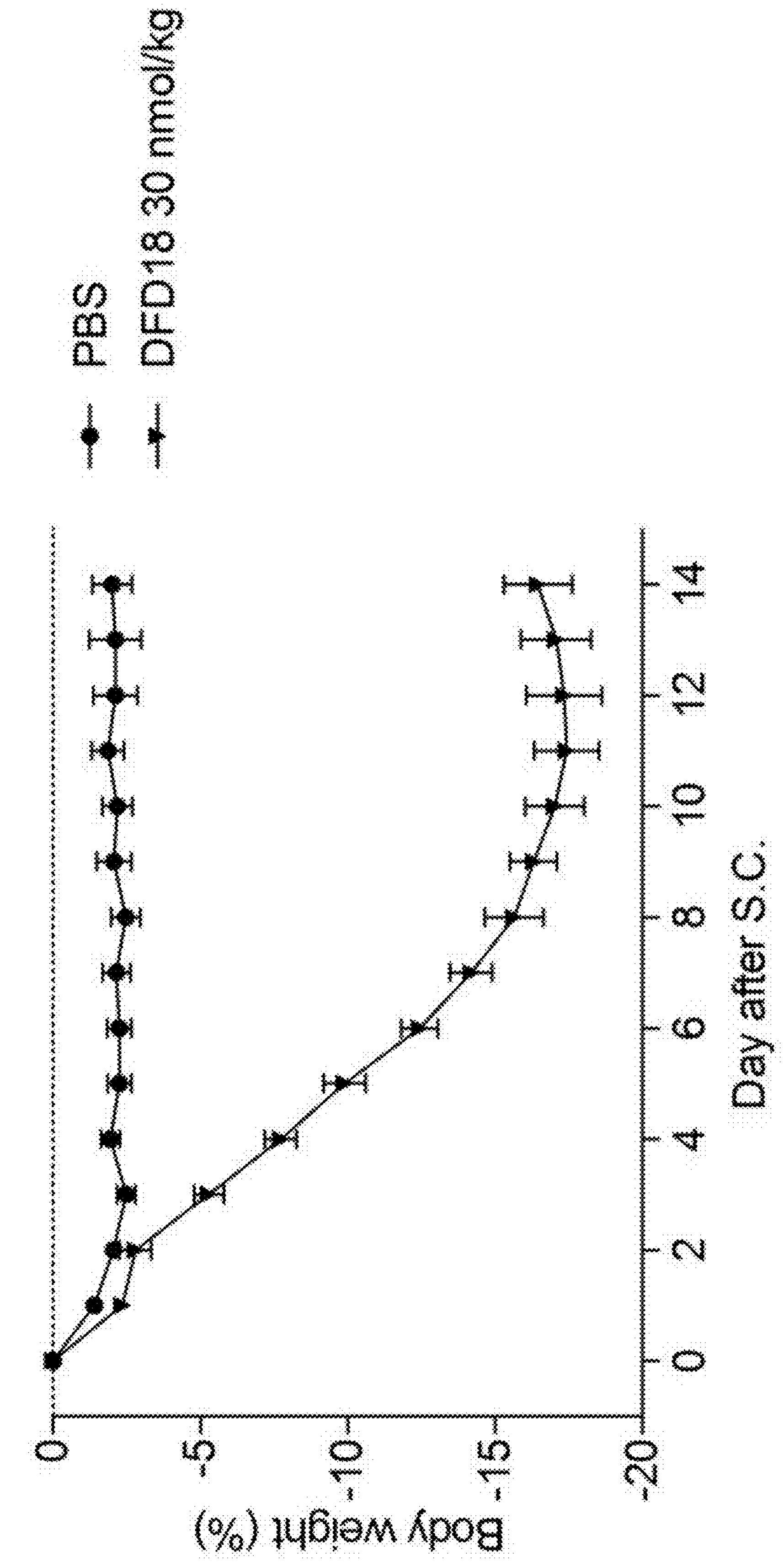

For changes in body weight over time in the diet-induced obesity mouse model following single administration of 30 nmol/kg DFD18, it was confirmed that the weight-reducing effect was continuing by the 10$^{th}$ day after the administration, and the maximum weight reduction (about 18%) was at the 11$^{th}$ day after the administration, which was maintained by the 14$^{th}$ day (FIGS. 12A and 12B).

Experimental Example 7. Prediction and Evaluation of Immunogenicity

Experimental Example 7-1. Method for Prediction of Immunogenicity and Results In order to predict the potential immunogenicity of FGF21 mutant fusion proteins, in silico analysis of immunogenicity was performed for each protein.

Specifically, the potential immunogenicity of the proteins was rapidly screened by using ITOPE™ and TCED™ methods (Prediction of immunogenicity of therapeutic proteins: validity of computational tools, BioDrugs, 2010). In regards to the two methods, the T-cell epitope may be more accurately predicted as compared with the in silico analytical method which depends on MHC class II binding analysis only.

Experimental Example 7-2. Ex Vivo Evaluation Method for Immunogenicity and Results In order to evaluate the potential immunogenicity of FGF21 mutant fusion proteins, EPISCREEN™ analysis (Increased brain bio-distribution and chemical stability and decreased immunogenicity of an engineered variant of GDNF, Exp Neurol, 2015) was performed. When immunogenicity is detected, the amino acid sequences inducing immunogenicity may be identified through T-cell epitope mapping, and deimmunized mutants with minimized immunogenicity may be designed and prepared via in silico prediction to reevaluate immunogenicity.

The invention claimed is:

1. A method for treating dyslipidemia, metabolic syndrome, non-alcoholic fatty liver disease or non-alcoholic steatohepatitis in a subject in need thereof, comprising administering a pharmaceutical composition to the subject, wherein the pharmaceutical composition comprises a fusion protein and a pharmaceutically acceptable carrier, wherein the fusion protein comprises a fibroblast growth factor 21 (FGF21) mutant protein connected via a linker to an Fc region of an immunoglobulin, wherein the FGF21 mutant protein comprises the following mutations:

(a)(1) a substitution of the amino acids at positions 98 to 101 from the N-terminus of a wild type FGF21 protein with the amino acid sequence of EIRP (SEQ ID NO: 42) and (a)(2) a substitution of the amino acid at position 180 from the N-terminus of a wild-type FGF21 protein with the amino acid E, along with one of the following mutations (b)-(d):

(b) a substitution of the amino acids at positions 170 to 174 from the N-terminus of a wild-type FGF21 protein with the amino acid sequence of TGLEAV (SEQ ID NO: 43); dfd18

(c) a substitution of the amino acids at positions 170 to 174 from the N-terminus of a wild-type FGF21 protein with the amino acid sequence of TGLEAN (SEQ ID NO: 44); and dfd73

(d) a substitution the amino acid at position 170 from the N-terminus of a wild-type FGF21 protein with the amino acid N, wherein the amino acid residue N of the FGF21 mutant protein in (c) and (d) is glycosylated.

2. A method selected from the group consisting of:

reducing blood glucose level in a subject;

reducing body weight in a subject;

reducing triglyceride or low-density lipoprotein levels in a subject; and improving insulin sensitivity in a subject wherein the method comprises administering a pharmaceutical composition to the subject, wherein the pharmaceutical composition comprises a fusion protein and a pharmaceutically acceptable carrier, wherein the fusion protein comprises a fibroblast growth factor 21 (FGF21) mutant protein connected via a linker to an Fc region of an immunoglobulin, wherein the FGF21 mutant protein comprises the following mutations:

(a)(1) a substitution of the amino acids at positions 98 to 101 from the N-terminus of a wild type FGF21 protein with the amino acid sequence of EIRP (SEQ ID NO: 42) and (a)(2) a substitution of the amino acid at position 180 from the N-terminus of a wild-type FGF21 protein with the amino acid E, along with one of the following mutations (b)-(d):

(b) a substitution of the amino acids at positions 170 to 174 from the N-terminus of a wild-type FGF21 protein with the amino acid sequence of TGLEAV (SEQ ID NO: 43);

(c) a substitution of the amino acids at positions 170 to 174 from the N-terminus of a wild-type FGF21 protein with the amino acid sequence of TGLEAN (SEQ ID NO: 44); and (d) a substitution the amino acid at position 170 from the N-terminus of a wild-type FGF21 protein with the amino acid N, wherein the amino acid residue N of the FGF21 mutant protein in (c) and (d) is glycosylated.

3. The method of claim 2, wherein the subject is obese.

4. The method of claim 2, wherein the subject has diabetes.

* * * * *